(12) United States Patent
Tipirneni et al.

(10) Patent No.: US 8,828,067 B2
(45) Date of Patent: Sep. 9, 2014

(54) BONE SCREW SYSTEM AND METHOD

(75) Inventors: Kishore Tipirneni, Glendale, AZ (US); Wayne Vassello, Lake Worth, FL (US)

(73) Assignee: Orthoip, LLC, Boca Raton, FL (US)

( * ) Notice: Subject to any disclaimer, the term of this patent is extended or adjusted under 35 U.S.C. 154(b) by 644 days.

(21) Appl. No.: 11/952,715

(22) Filed: Dec. 7, 2007

(65) Prior Publication Data

US 2008/0147127 A1    Jun. 19, 2008

Related U.S. Application Data

(63) Continuation-in-part of application No. 11/742,457, filed on Apr. 30, 2007, which is a continuation-in-part of application No. 11/678,473, filed on Feb. 23, 2007, which is a continuation-in-part of application No. 10/779,892, filed on Feb. 17, 2004, which is a continuation of application No. 10/272,773, filed on Oct. 17, 2002, now Pat. No. 6,736,819.

(60) Provisional application No. 60/330,187, filed on Oct. 18, 2001.

(51) Int. Cl.
- *A61B 17/58* (2006.01)
- *A61B 17/74* (2006.01)
- *A61B 17/86* (2006.01)
- *A61B 17/88* (2006.01)

(52) U.S. Cl.
CPC ......... *A61B 17/8685* (2013.01); *A61B 17/8625* (2013.01); *A61B 17/746* (2013.01); *A61B 17/8877* (2013.01); *A61B 17/8869* (2013.01); *A61B 17/8863* (2013.01); *A61B 17/861* (2013.01); *A61B 17/742* (2013.01); *A61B 17/744* (2013.01)
USPC ....................................................... 606/320

(58) Field of Classification Search
USPC ............... 606/300, 304, 65, 66, 67, 109, 310, 606/328, 320
See application file for complete search history.

(56) References Cited

U.S. PATENT DOCUMENTS

| 1,025,008 A | 4/1912 | Miner | |
|---|---|---|---|
| 1,895,845 A * | 1/1933 | Halloy | .......................... 411/107 |

(Continued)

FOREIGN PATENT DOCUMENTS

| FR | 2784019 | 4/2000 |
|---|---|---|
| GB | 2136688 | 9/1994 |

(Continued)

OTHER PUBLICATIONS

Notice of Allowance mailed Feb. 20, 2004 in U.S. Appl. No. 10/272,773.

(Continued)

*Primary Examiner* — Christian Sevilla
(74) *Attorney, Agent, or Firm* — Snell & Wilmer L.L.P.

(57) ABSTRACT

An improved bone screw is disclosed which includes a shaft with distal portion having a threaded surface thereon, a sleeve having an opening which receives the shaft such that the shaft is able to move within the sleeve without moving the sleeve. A compressive device may be incorporated between the sleeve and the proximal portion of the shaft such that the compressive device forces the shaft and sleeve towards at least a portion each other, thereby maintaining the compressive load at the union of the fracture. As additional compression is exerted on the load from weight bearing, the force may be reduced, but the head of the sleeve is still substantially maintained against the lateral cortex.

11 Claims, 19 Drawing Sheets

(56) References Cited

U.S. PATENT DOCUMENTS

| | | | |
|---|---|---|---|
| 2,077,804 A | 4/1937 | Morrison | |
| 2,381,050 A | 8/1945 | Hardinge | |
| 2,397,545 A | 4/1946 | Hardinge | |
| 2,414,882 A | 1/1947 | Longfellow | |
| 2,490,364 A | 12/1949 | Livingston | |
| 2,511,051 A | 6/1950 | Dzus | |
| 2,586,556 A * | 2/1952 | Mullikin | 411/339 |
| 3,051,169 A * | 8/1962 | Grath | 606/65 |
| 3,433,220 A | 3/1969 | Zickel | |
| 3,489,143 A * | 1/1970 | Halloran | 606/67 |
| 4,341,206 A * | 7/1982 | Perrett et al. | 606/80 |
| 4,432,358 A * | 2/1984 | Fixel | 606/66 |
| 4,456,005 A | 6/1984 | Lichty | |
| 4,617,922 A | 10/1986 | Griggs | |
| 4,621,629 A * | 11/1986 | Koeneman | 606/65 |
| 4,632,100 A | 12/1986 | Somers et al. | |
| 4,640,271 A * | 2/1987 | Lower | 606/65 |
| 4,688,561 A | 8/1987 | Reese | |
| 4,708,132 A | 11/1987 | Silvestrini | |
| 4,741,330 A | 5/1988 | Hayhurst | |
| 4,773,406 A | 9/1988 | Spector et al. | |
| 4,858,601 A | 8/1989 | Gisson | |
| 4,863,383 A | 9/1989 | Grafelmann | |
| 4,889,110 A | 12/1989 | Galline | |
| 4,905,680 A | 3/1990 | Tunc | |
| 4,934,935 A | 6/1990 | Edwards | |
| 4,940,467 A * | 7/1990 | Tronzo | 606/66 |
| 4,959,064 A * | 9/1990 | Engelhardt | 606/65 |
| 5,019,079 A | 5/1991 | Ross | |
| 5,041,116 A | 8/1991 | Wilson | |
| 5,061,137 A * | 10/1991 | Gourd | 411/510 |
| 5,100,405 A * | 3/1992 | McLaren | 606/304 |
| 5,102,276 A * | 4/1992 | Gourd | 411/392 |
| 5,116,336 A | 5/1992 | Frigg | |
| 5,116,340 A | 5/1992 | Songer | |
| 5,122,133 A * | 6/1992 | Evans | 606/301 |
| 5,127,914 A | 7/1992 | Calderale et al. | |
| 5,129,901 A * | 7/1992 | Decoste | 606/65 |
| 5,141,520 A | 8/1992 | Goble et al. | |
| 5,207,753 A | 5/1993 | Badrinath | |
| 5,217,462 A | 6/1993 | Asnis et al. | |
| 5,269,784 A | 12/1993 | Mast | |
| 5,300,075 A | 4/1994 | Gordon | |
| 5,306,290 A | 4/1994 | Martins et al. | |
| 5,324,292 A | 6/1994 | Meyers | |
| 5,336,028 A | 8/1994 | Yamamoto | |
| 5,338,139 A | 8/1994 | Swanstrom | |
| 5,364,398 A | 11/1994 | Chapman et al. | |
| 5,368,605 A | 11/1994 | Miller | |
| 5,382,124 A | 1/1995 | Frattarola | |
| 5,409,493 A | 4/1995 | Greenberg | |
| 5,417,692 A | 5/1995 | Goble et al. | |
| 5,423,820 A | 6/1995 | Miller et al. | |
| 5,431,660 A | 7/1995 | Burke | |
| 5,462,547 A | 10/1995 | Weigum | |
| 5,507,801 A | 4/1996 | Gisin | |
| 5,520,691 A | 5/1996 | Branch | |
| 5,529,075 A | 6/1996 | Clark | |
| 5,586,985 A | 12/1996 | Putnam et al. | |
| 5,591,207 A | 1/1997 | Coleman | |
| 5,601,553 A | 2/1997 | Trebing et al. | |
| 5,607,426 A | 3/1997 | Ralph et al. | |
| 5,611,801 A | 3/1997 | Songer | |
| 5,632,745 A | 5/1997 | Schwartz | |
| 5,643,267 A | 7/1997 | Hitomi et al. | |
| 5,702,397 A | 12/1997 | Goble et al. | |
| 5,709,687 A | 1/1998 | Penning | |
| 5,725,582 A | 3/1998 | Bevan | |
| 5,743,912 A | 4/1998 | Lahille et al. | |
| 5,809,849 A | 9/1998 | Coffey et al. | |
| 5,810,821 A | 9/1998 | Vandewalle | |
| 5,827,285 A * | 10/1998 | Bramlet | 606/60 |
| 5,893,850 A | 4/1999 | Cachia | |
| 5,893,859 A | 4/1999 | Marin et al. | |
| 5,899,906 A | 5/1999 | Schenk | |
| 5,902,011 A | 5/1999 | Hand et al. | |
| 5,928,236 A | 7/1999 | Augagneur et al. | |
| 5,954,722 A | 9/1999 | Bono | |
| 5,964,760 A | 10/1999 | Richelsoph | |
| 5,964,763 A | 10/1999 | Incavo et al. | |
| 5,976,139 A | 11/1999 | Bramlet | |
| 5,984,925 A | 11/1999 | Apgar | |
| 5,993,477 A | 11/1999 | Vaitekunas et al. | |
| 5,997,538 A | 12/1999 | Asnis et al. | |
| 5,997,541 A * | 12/1999 | Schenk | 606/303 |
| 6,027,523 A | 2/2000 | Schmieding | |
| 6,033,429 A | 3/2000 | Magovern | |
| 6,039,740 A | 3/2000 | Olerud | |
| 6,050,998 A | 4/2000 | Fletcher | |
| 6,093,188 A | 7/2000 | Murray | |
| 6,143,037 A | 11/2000 | Goldstein et al. | |
| 6,171,310 B1 | 1/2001 | Giordano | |
| 6,174,006 B1 | 1/2001 | Burt | |
| 6,174,312 B1 | 1/2001 | Laminger | |
| 6,179,537 B1 * | 1/2001 | Anders | 411/392 |
| 6,183,474 B1 | 2/2001 | Bramlet | |
| 6,235,062 B1 | 5/2001 | Grammas | |
| 6,245,071 B1 | 6/2001 | Pierson | |
| 6,251,111 B1 | 6/2001 | Barker et al. | |
| 6,261,291 B1 | 7/2001 | Talaber et al. | |
| 6,319,254 B1 | 11/2001 | Giet et al. | |
| 6,348,053 B1 | 2/2002 | Cachia | |
| 6,368,326 B1 | 4/2002 | Dakin et al. | |
| 6,524,313 B1 | 2/2003 | Fassier et al. | |
| 6,602,293 B1 | 8/2003 | Biermann et al. | |
| 6,605,090 B1 | 8/2003 | Trieu et al. | |
| 6,610,067 B2 | 8/2003 | Tallarida et al. | |
| 6,629,534 B1 | 10/2003 | St Goar et al. | |
| 6,632,224 B2 * | 10/2003 | Cachia et al. | 606/304 |
| 6,656,184 B1 | 12/2003 | White et al. | |
| 6,656,185 B2 | 12/2003 | Gleason et al. | |
| 6,685,706 B2 | 2/2004 | Padget et al. | |
| 6,695,844 B2 | 2/2004 | Bramlet | |
| 6,736,819 B2 | 5/2004 | Tipirneni | |
| 6,840,953 B2 | 1/2005 | Martinek | |
| 6,887,243 B2 | 5/2005 | Culbert | |
| 6,887,271 B2 | 5/2005 | Justin et al. | |
| 6,890,333 B2 | 5/2005 | von Hoffmann et al. | |
| 6,902,567 B2 | 6/2005 | Del Medico | |
| 6,908,465 B2 | 6/2005 | von Hoffmann et al. | |
| 6,984,241 B2 | 1/2006 | Lubbers | |
| 7,008,428 B2 | 3/2006 | Cachia et al. | |
| 7,033,363 B2 | 4/2006 | Powell | |
| 7,070,601 B2 | 7/2006 | Culbert et al. | |
| 7,090,676 B2 | 8/2006 | Huebner et al. | |
| 7,094,239 B1 | 8/2006 | Michelson | |
| 7,094,240 B2 | 8/2006 | Molz et al. | |
| 7,135,023 B2 | 11/2006 | Watkins | |
| 7,147,639 B2 | 12/2006 | Berki et al. | |
| 7,163,542 B2 | 1/2007 | Ryan | |
| 7,172,595 B1 | 2/2007 | Goble | |
| 7,189,251 B2 | 3/2007 | Kay | |
| 7,476,254 B2 * | 1/2009 | White et al. | 623/22.32 |
| 7,591,823 B2 | 9/2009 | Tipirneni | |
| 7,641,677 B2 | 1/2010 | Weiner et al. | |
| 7,771,428 B2 | 8/2010 | Siravo et al. | |
| 2002/0198527 A1 | 12/2002 | Muckter | |
| 2003/0036761 A1 | 2/2003 | Smothers et al. | |
| 2003/0083658 A1 | 5/2003 | Hawkes et al. | |
| 2003/0187440 A1 | 10/2003 | Richelsoph et al. | |
| 2003/0216780 A1 | 11/2003 | Fitts et al. | |
| 2004/0097943 A1 | 5/2004 | Hart | |
| 2004/0127906 A1 * | 7/2004 | Culbert et al. | 606/72 |
| 2004/0236424 A1 | 11/2004 | Berez et al. | |
| 2004/0243129 A1 | 12/2004 | Moumene et al. | |
| 2005/0010226 A1 | 1/2005 | Grady, Jr. et al. | |
| 2005/0143735 A1 * | 6/2005 | Kyle | 606/60 |
| 2005/0234456 A1 | 10/2005 | Malandain | |
| 2005/0240190 A1 * | 10/2005 | Gall et al. | 606/72 |
| 2005/0245933 A1 | 11/2005 | Sevrain | |
| 2005/0263549 A1 | 12/2005 | Scheiner | |
| 2005/0277940 A1 * | 12/2005 | Neff | 606/73 |
| 2006/0129148 A1 | 6/2006 | Simmons et al. | |
| 2006/0147127 A1 | 7/2006 | Slavin | |

(56) References Cited

U.S. PATENT DOCUMENTS

| | | | |
|---|---|---|---|
| 2006/0155297 A1* | 7/2006 | Ainsworth et al. | 606/99 |
| 2006/0161805 A1 | 7/2006 | Tseng | |
| 2006/0167457 A1 | 7/2006 | Suddaby | |
| 2006/0190001 A1 | 8/2006 | Powell | |
| 2006/0248638 A1 | 11/2006 | Deithelm et al. | |
| 2006/0264954 A1* | 11/2006 | Sweeney et al. | 606/73 |
| 2007/0055249 A1 | 3/2007 | Jensen et al. | |
| 2007/0123878 A1 | 5/2007 | Shaver | |
| 2007/0162019 A1 | 7/2007 | Burns et al. | |
| 2007/0162026 A1 | 7/2007 | Tipirneni et al. | |
| 2007/0190230 A1 | 8/2007 | Trieu | |
| 2007/0233100 A1 | 10/2007 | Metzinger | |
| 2007/0260248 A1 | 11/2007 | Tipirneni | |
| 2007/0270847 A1 | 11/2007 | Shaw | |
| 2007/0270855 A1 | 11/2007 | Partin | |
| 2007/0276382 A1 | 11/2007 | Mikhail et al. | |
| 2008/0086144 A1 | 4/2008 | Zander | |
| 2008/0147126 A1 | 6/2008 | Tipirneni | |
| 2008/0147127 A1 | 6/2008 | Tipirneni et al. | |
| 2008/0243191 A1 | 10/2008 | Tipirneni et al. | |
| 2008/0255555 A1 | 10/2008 | Justis et al. | |
| 2008/0255621 A1 | 10/2008 | Fricker et al. | |
| 2008/0269746 A1 | 10/2008 | Justin | |
| 2008/0300636 A1 | 12/2008 | Carli et al. | |
| 2009/0131936 A1 | 5/2009 | Tipirneni et al. | |
| 2009/0131990 A1 | 5/2009 | Tipirneni et al. | |
| 2009/0131991 A1 | 5/2009 | Tipirneni et al. | |
| 2009/0177199 A1 | 7/2009 | Tipirneni | |
| 2009/0198288 A1 | 8/2009 | Hoof et al. | |
| 2009/0254089 A1 | 10/2009 | Tipirneni | |
| 2009/0254129 A1 | 10/2009 | Tipirneni | |
| 2009/0306718 A1 | 12/2009 | Tipirneni | |
| 2010/0114097 A1 | 5/2010 | Siravo et al. | |
| 2010/0312245 A1 | 12/2010 | Tipirneni et al. | |
| 2010/0312292 A1 | 12/2010 | Tipirneni et al. | |
| 2011/0034925 A1 | 2/2011 | Tipirneni et al. | |
| 2011/0295252 A1 | 12/2011 | Tipirneni et al. | |

FOREIGN PATENT DOCUMENTS

| | | |
|---|---|---|
| GB | 2323533 | 9/1998 |
| WO | WO0067652 | 11/2000 |
| WO | WO2007125561 | 11/2008 |
| WO | WO 2009/150175 | 12/2009 |

OTHER PUBLICATIONS

Non-Final Office Action mailed Nov. 16, 2005 in U.S. Appl. No. 10/779,892.
Requirement for Restriction mailed Jul. 18, 2006 in U.S. Appl. No. 10/779,892.
Final Office Action mailed Jan. 3, 2007 in U.S. Appl. No. 10/779,892.
Advisory Action mailed Feb. 2, 2007 in U.S. Appl. No. 10/779,892.
Non-Final Office Action mailed Mar. 1, 2007 in U.S. Appl. No. 10/779,892.
Final Office Action mailed Oct. 31, 2007 in U.S. Appl. No. 10/779,892.
Advisory Action mailed Jan. 22, 2008 in U.S. Appl. No. 10/779,892.
Non-Final Office Action mailed Mar. 4, 2008 in U.S. Appl. No. 10/779,892.
Requirement for Restriction mailed Dec. 10, 2008 in U.S. Appl. No. 10/779,892.
ISR and Written Opinion mailed Jan. 22, 2009 in PCT/US08/84623.
Final Office Action mailed May 14, 2009 in U.S. Appl. No. 10/779,892.
Notice of Allowance mailed Aug. 7, 2009 in U.S. Appl. No. 10/779,892.
Non-Final Office Action mailed Aug. 6, 2009 in U.S. Appl. No. 11/742,457.
Non-Final Office Action mailed Jun. 10, 2009 in U.S. Appl. No. 11/952,413.
Non-Final Office Action mailed Aug. 20, 2009 in U.S. Appl. No. 11/678,473.
USPTO; Notice of Allowance dated Dec. 14, 2010 in U.S. Appl. No. 12/400,184.
PCT; International Preliminary Report on Patentability dated Jul. 15, 2010 in Application No. PCT/US2008/084623.
Final Office Action dated Dec. 7, 2011 in U.S. Appl. No. 12/235,405.
Final Office Action dated Feb. 1, 2012 in U.S. Appl. No. 12/265,890.
Office Action dated Apr. 27, 2011 in U.S. Appl. No. 12/400,165.
Office Action dated May 11, 2011 in U.S. Appl. No. 12/369,589.
Final Office Action mailed Feb. 19, 2010 in U.S. Appl. No. 11/678,473.
Advisory Acton mailed Apr. 14, 2010 in U.S. Appl. No. 11/678,473.
Final Office Action mailed Jan. 22, 2010 in U.S. Appl. No. 11/741,457.
Advisory Action mailed on Mar. 30, 2010 in U.S. Appl. No. 11/741,457.
Notice to File Missing Parts on May 12, 2010 in U.S. Appl. No. 12/769,529.
Non-Final Office Action issued Dec. 30, 2009 in U.S. Appl. No. 11/952,413.
PCT/US2009/061782 International Search Report and Written Opinion issued Dec. 15, 2009.
PCT/US09/578791 International Search Report and Written Opinion issued Nov. 16, 2009.
URL: http://www.cayennemedical.com/products/ifix/, Title: iFix, Source: Cayenne Medical in U.S. Appl. No. 12/265,890.
PCT-US2010-023537 International Search and Written Opinion Report mailed Apr. 15, 2010.
International Preliminary Report on Patentability dated Jul. 20, 2011 in Application No. PCT/US2010/023537.
Office Action dated Jun. 22, 2011 in U.S. Appl. No. 12/235,405.
Office Action Restriction dated Jun. 22, 2011 in U.S. Appl. No. 12/163,122.
Final Office Action dated Aug. 16, 2011 in U.S. Appl. No. 12/104,328.
Office Action dated Aug. 17, 2011 in U.S. Appl. No. 12/163,122.
Office Action dated Aug. 19, 2011 in U.S. Appl. No. 12/265,890.
Non-Final Office Action issued Jun. 28, 2010 in U.S. Appl. No. 12/400,184.
Final Office Action issued Jun. 29, 2010 in U.S. Appl. No. 11/952,413.
Advisory Action issued Sep. 1, 2010 in U.S. Appl. No. 11/952,413.
PCT International Search Report and Written Opinion dated Jan. 22, 2009.
International Search Report and Written Opinion dated Jul. 7, 2011 in Application No. PCT/US2011/033370.
Notice of Allowance dated Sep. 29, 2011 in U.S. Appl. No. 12/400,165.
Final Office Action dated Oct. 28, 2011 in U.S. Appl. No. 12/369,589.
Office Action dated Nov. 1, 2011 in U.S. Appl. No. 12/425,225.
Office Action dated Nov. 10, 2011 in U.S. Appl. No. 12/491,132.
Office Action dated Nov. 10, 2011 in U.S. Appl. No. 12/258,013.
Office Action dated Sep. 2, 2011 in U.S. Appl. No. 12/104,658.
International Preliminary Report on Patentability dated Jan. 31, 2011 in Application No. PCT/US2009/061782.
International Preliminary Report on Patentability dated Jan. 31, 2011 in Application No. PCT/US2009/057879.
Office Action dated Mar. 17, 2011 in U.S. Appl. No. 12/104,658.
Office Action dated Mar. 8, 2011 in U.S. Appl. No. 12/104,328.
International Search Report and Written Opinion dated Feb. 23, 2012 in Application No. PCT/US2011/048192.
Office Action dated Apr. 6, 2012 in U.S. Appl. No. 12/769,529.
Restriction Requirement dated Apr. 9, 2012 in U.S. Appl. No. 12/860,122.
Restriction Requirement dated Apr. 9, 2012 in U.S. Appl. No. 12/898,975.
Restriction Requirement dated Apr. 25, 2012 in U.S. Appl. No. 12/860,178.

(56) References Cited

OTHER PUBLICATIONS

Final Office Action dated Jun. 5, 2012 in U.S. Appl. No. 12/425,225.

International Preliminary Report on Patentability dated Mar. 7, 2013 in Application No. PCT/US2011/048192.

Restriction Requirement dated Mar. 28, 2013 in U.S. Appl. No. 13/118,871.

Supplementary Search Report dated Apr. 9, 2013 in European Application No. 08858204.4.

Office Action dated Apr. 9, 2013 in U.S. Appl. No. 11/952,413.

Notice of Allowance dated Nov. 6, 2013 in U.S. Appl. No. 11/678,473.

Notice of Allowance dated Nov. 6, 2013 in U.S. Appl. No. 11/742,457.

Biomet, OptiLock? Periarticular Plating System for Distal Femoral Fractures, Pre-Launch 1-10 Surgical Technique, Aug. 2007, retrieved on Feb. 10, 2012, Retrieved from the Internet:<URL: http://www.biomet.co.uk/resource/2051/Distal%20Femoral%20Surgical%20Tech_FINAL_8.01.07.pdf, pp. 1-28.

* cited by examiner

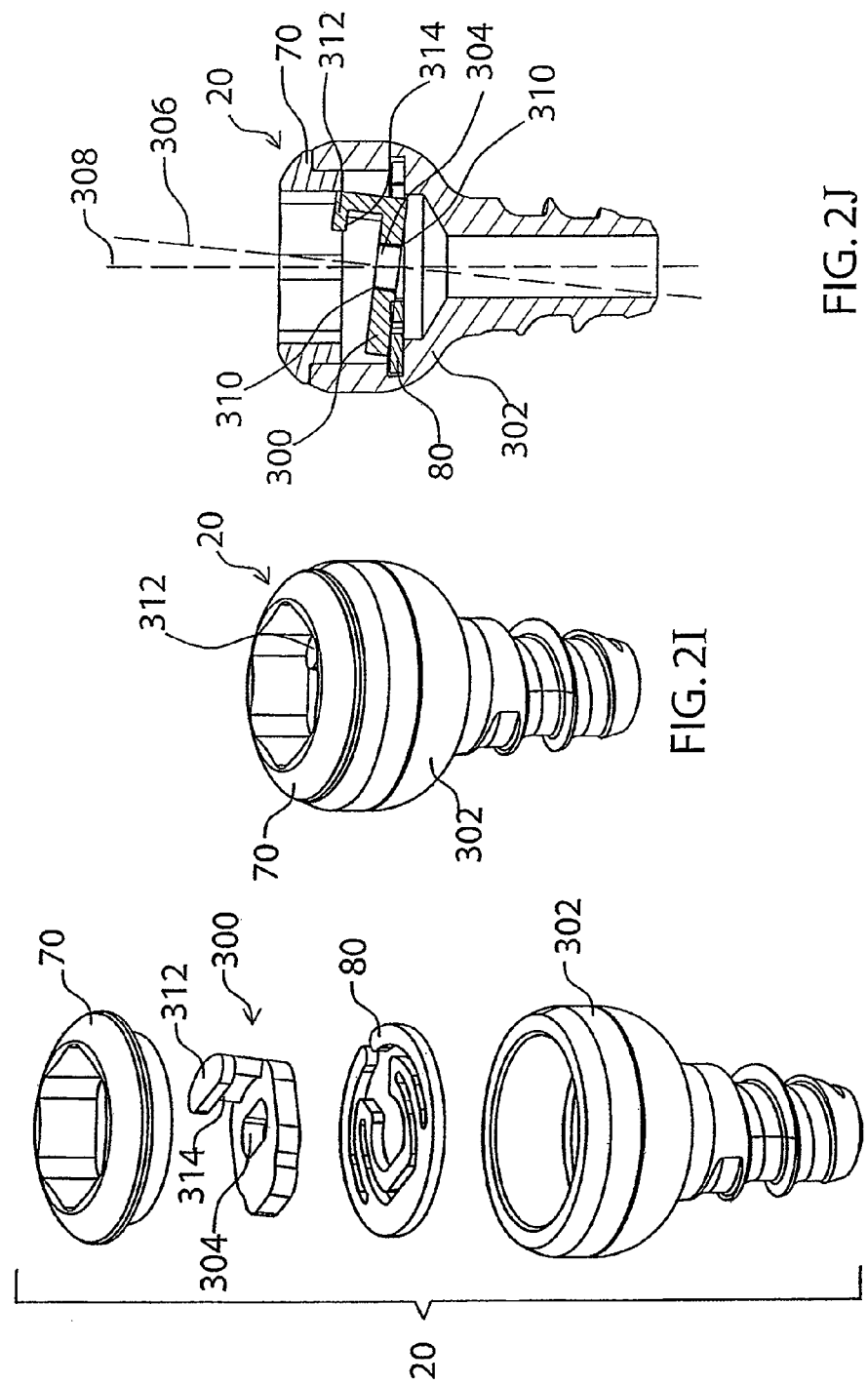

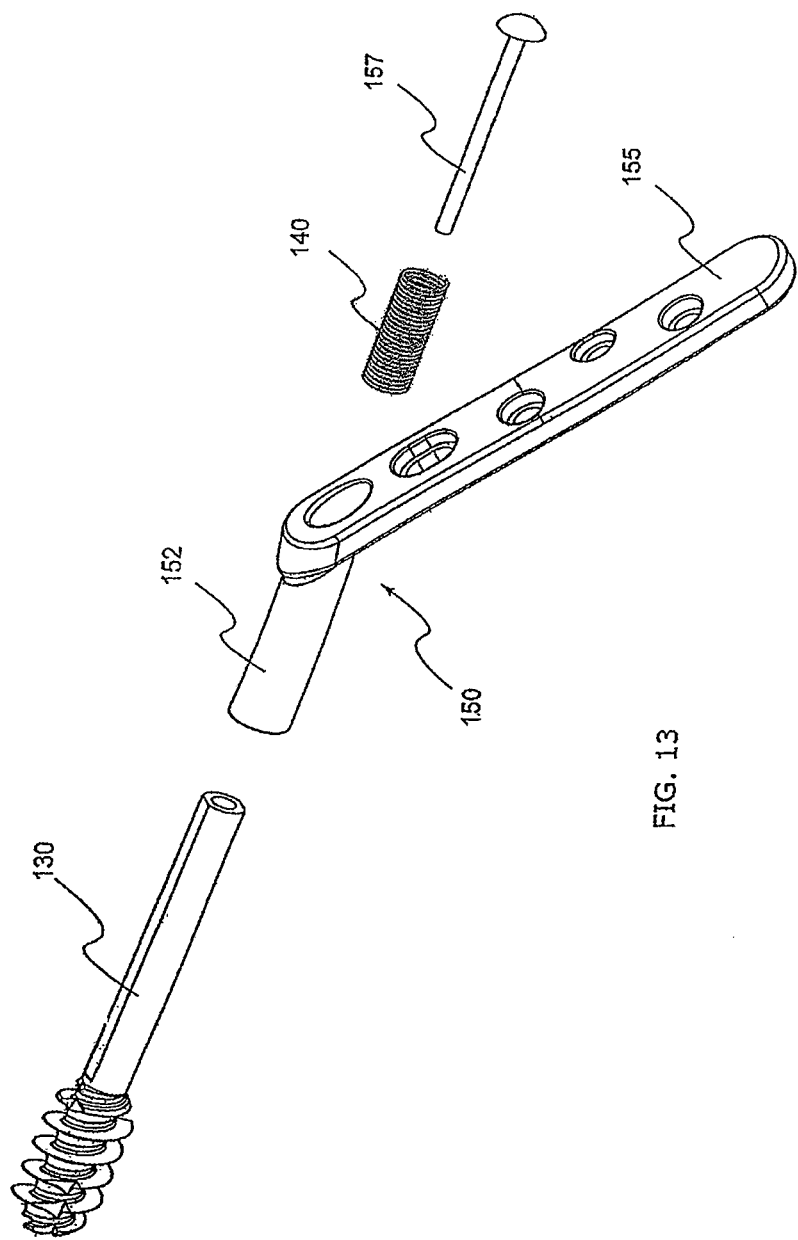

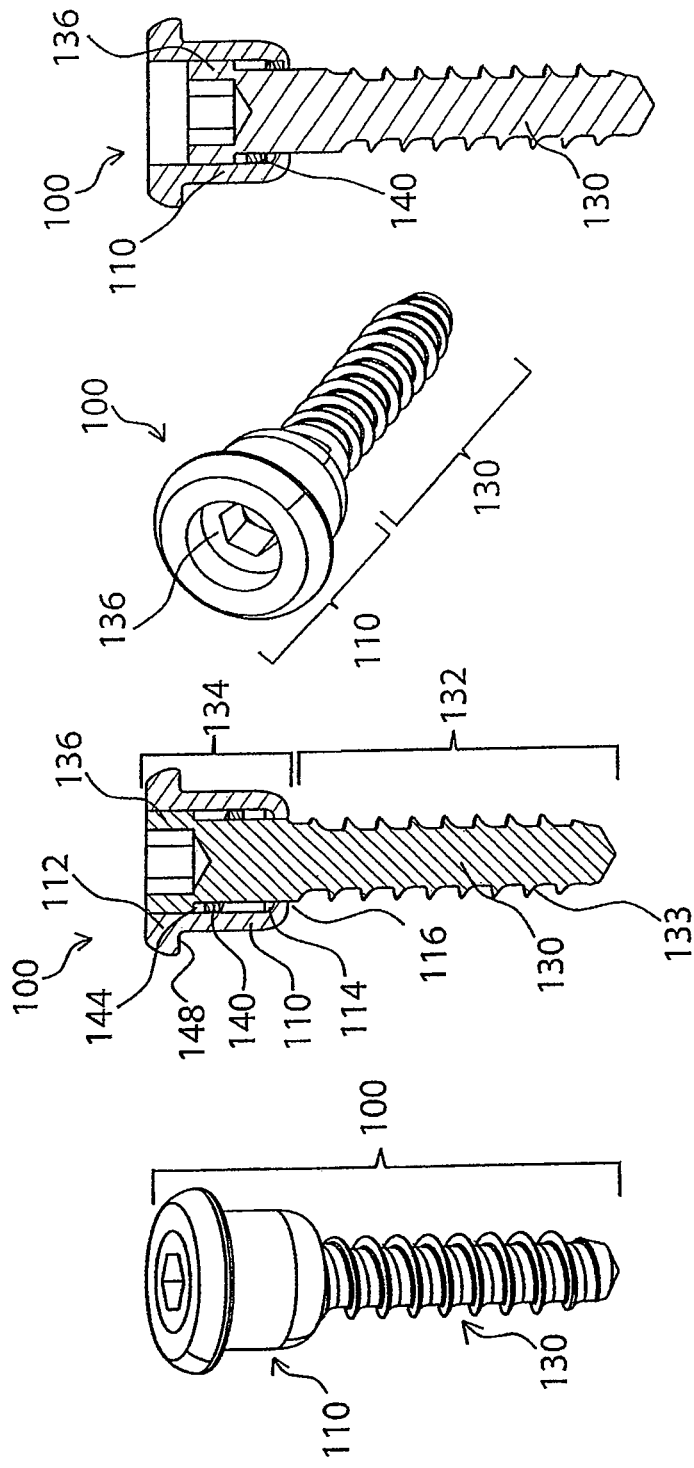

BONE SCREW SYSTEM AND METHOD

CROSS-REFERENCE TO RELATED APPLICATIONS

This application is a continuation-in-part of, and claims priority to, U.S. Ser. No. 11/742,457, filed on Apr. 30, 2007 and entitled CANNULATED BONE SCREW SYSTEM AND METHOD which itself is a continuation-in-part of, and claims priority to, U.S. Ser. No. 11/678,473, filed on Feb. 23, 2007 and entitled SYSTEM AND METHOD FOR A CAP USED IN THE FIXATION OF BONE FRACTURES which itself is a continuation-in-part of, and claims priority to, U.S. Ser. No. 10/779,892, filed on Feb. 17, 2004 and entitled SYSTEM AND METHOD FOR THE FIXATION OF BONE FRACTURES which itself claims priority to U.S. Ser. No. 10/272,773, filed on Oct. 17, 2002 with the same title (now U.S. Pat. No. 6,736,819). The '819 patent itself claims priority to U.S. Provisional Application Ser. No. 60/330,187, filed on Oct. 18, 2001 and entitled LAGWIRE SYSTEM AND METHOD. All of the above-mentioned patents and applications are incorporated herein by reference.

FIELD OF INVENTION

The invention generally relates to a system and method for the fixation of fractures in one or more objects, which may be separate objects or separate object portions or fragments of the same object, and more particularly, to a bone screw for the fixation of bone fractures which collapses along with the fracture collapse to minimize protrusion of the device beyond the bone surface, and to maintain compression across the fracture during fracture collapse.

BACKGROUND OF THE INVENTION

It is well-known in the medical arts that constant pressure on a bone fracture speeds healing. As such, orthopedic physicians typically insert one or more screws in the area of the fracture in order to assert constant pressure on the bone fracture. However, the insertion of existing screws through or around fractures has disadvantages. For example, the entire process is very time-consuming because inserting a regular screw usually involves multiple steps such as drilling the pilot hole, measuring the relevant distances to determine the appropriate screw selection, tapping the hole to establish threads and screwing the screw into the hole. Moreover, when using a bone screw, the process usually includes even more steps such as drilling through the near cortex to establish the guiding hole (e.g., 3.5 mm), placing the drill guide in the proper location, drilling through the far cortex (e.g., 2.5 mm), measuring the distance to determine the appropriate screw selection, tapping the hole to establish threads and rotating the screw into the hole, thereby attempting to compress the fracture. Again, each step and the entire process is very time-consuming.

In addition to the length and complexity of the process, the prior art system also typically includes inadequate components. For example, in poor bone, prior art screws often loose their grip and strip out of the bone. Currently available bone screws also typically provide only one side of cortex fixation and are generally not suited for percutaneous surgery. Moreover, when placing the screws in the bone, the physician may not accurately set the screw into the distal hole or may miss the distal hole completely, thereby resulting in the screw stripping the threads or breaking the bone.

Furthermore, the location and extent of most every fracture is unique, so different screws are often needed for each fracture. Because the physician typically is unable to accurately determine the type or size of screw needed until the physician enters the bone and measures the appropriate screw placement, operating facilities need to store and make available large inventories of screws. Particularly, screws usually range in length from about 10 mm to about 75 mm with available screw sizes limited to every 2 mm there between. Moreover, for each size of screw, the screws may be either a cancellous or cortical type, and for each size and type of screw, the screw may include one of three different pitches. Accordingly, a screw set typically exceeds one hundred screws. Furthermore, if cannulated screws are desired, another entire screw set of over one hundred additional screws is often needed. Moreover, each time a screw from a screw set is utilized in a procedure, a replacement screw is typically obtained to complete the set. As such, inventory management of screws is a very large problem for many operating facilities. A need exists for a lagwire system which simplifies and expedites the process for the fixation of bone fractures, while minimizing the number of components needed in the process.

Additionally, in hip fractures (e.g. femoral neck fracture), the non-union rate is about 25-30%. Certain factors may contribute to the non-union rate in fractures such as, for example, poor blood supply and age of patient. However, an important factor for the non-union rate in fractures is micro-motion. Micro-motion of the hip bones is typically caused by the natural movements of the patient while the patient is walking, hopping on crutches, twisting and the like. Such micro-motion has an affect on the bone screw in that the micro-motion often causes the bone screw to slide within the bone, thereby disrupting the bone union. The bone union is disrupted because the union loses its fixed compression and fracture interface is decompressed.

Another concern with bone screws is that the head of bone screw often protrudes out of the bone surface over time. In particular, when a bone fracture is set with a bone screw, the bone screw typically does not completely compress the bone together. As such, after the patient stands and a weight bearing force is applied against the bone (or any other compressive forces applied to the bone), the bone is further compressed. The further compression of the bone or its portions or fragments results in the head of the bone screw (which was previously flush with the outside surface of the bone) protruding outside from the surface of the bone. In some cases, the head of the bone screw may protrude about 1 cm which may result in pain and/or the need for additional surgery. A need exists for a device and method for maintaining the initial and subsequent compression of a bone fracture to increase the union rate of the bone fracture.

SUMMARY OF THE INVENTION

In general, the invention facilitates the fixation of bone fractures. In one embodiment, a head or anchor component includes a tip, cutting threads and mating threads which are inserted into the far cortex of the bone. A wire extends from the anchor component and exits from the near cortex.

A cap device fits over the other end of the wire such that the cap device permits travel of the cap in one direction (e.g., distal travel with respect to the wire), but resists travel of the cap in the other direction (e.g., proximal travel with respect to the wire). In one embodiment, a cap device having a sawtooth inner surface is threaded over the wire having an inverse sawtooth outer surface such that the cap is restricted from backwards movement. In another embodiment, the cap includes a circular tension spring inside the cap such that the wire is received within a central opening within the circular tension spring. The tension spring also includes a nub extending from the outer circumference of the tension spring such that a portion of the inner circumference of the tension spring provides friction against the wire only one way (when the cap is pulled proximal, away from the bone). The friction is asserted against the wire because the nub on the side of the tension spring hits the top circular cap, so it forces the tension spring to flex and assert friction on the wire. When the cap is pushed the other way (e.g., when the cap is pushed distal, toward the bone) the nub of the tension spring is forced down, so it does not engage any surface, and the wire is able to translate, with minimal or no friction, through the central opening in the tension spring.

Tension is then applied to the wire while the cap is tightened against or within the bone surface to thereby apply an appropriate amount of pressure between the surfaces of the fracture. The excess wire beyond the cap can then be removed.

The invention also includes a system for facilitating a change in distance between objects, or object portions, wherein the system includes a anchor component configured to attach to one of the objects; a wire having a first end and a second end, wherein the first end of the wire is configured to mate with the anchor component; and, a cap configured to mate with the second end of the wire. The invention also includes a method for facilitating a change in distance between a first and second surface The method includes providing a anchor component mated with a wire having a first interface component; inserting the anchor component into the first surface by mating a drill over a driver head of the anchor component to facilitate drilling the anchor component into the bone and cutting new threads into the object using the cutting threads and mating the new threads with the mating threads; extending the wire through the second surface; threading a cap having a second interface component over the first interface component of the wire; and removing the excess wire beyond the cap.

In another embodiment, the invention includes a shaft with distal portion having a threaded surface thereon, a sleeve having an opening which receives the shaft such that the shaft is able to move within the sleeve with minimal or no movement of the sleeve. In one embodiment, a compressive device (e.g., spring, split washer, sponge, rubber bumper, resilient material or mechanism, etc.) may exist between the sleeve and the proximal portion of the shaft such that the compressive device exerts a force directly or indirectly against the shaft and the sleeve. In one embodiment, the compressive device is located inside the sleeve. The compressive device exerts a force which serves to move the distal head and the proximal sleeve toward each other, thereby maintaining the compressive load at the union of the fracture. As additional compression is exerted on the fracture from weight bearing, the force may be reduced, but the head of the sleeve is still substantially maintained against the lateral cortex and the proximal portion of the shaft is still substantially maintained within the sleeve. The sleeve may be maintained against or within the lateral cortex until sufficient collapse of the fracture occurs such that the compressive device no longer exerts a force against the sleeve or shaft, then the device may simply act as a traditional bone screw. As such, the improved bone screw of the present invention minimizes or prevents the device from protruding beyond the bone, and maintains the compression across the fracture during fracture collapse. The bone screw of the present invention may be used in place of any existing bone screw, or any existing component of a product that performs a similar function as a bone screw.

BRIEF DESCRIPTION OF THE DRAWINGS

A more complete understanding of the present invention may be derived by referring to the detailed description and claims when considered in connection with the figures, wherein like reference numbers refer to similar elements throughout the figures, and:

FIG. 2H is an exploded perspective view a cap in accordance with an exemplary embodiment of the present invention.

FIG. 2I is a perspective view of the embodiment of the cap of FIG. 2H, fully assembled.

FIG. 2J is a cross section view of the embodiment of the cap shown in FIG. 2I.

FIG. 13 shows another embodiment of a cannulated screw wherein the barrel functions as the sleeve, as part of a hip screw plate system, in accordance with an exemplary embodiment of the present invention.

FIG. 14 is a sleeve and a bone screw capable of receding within the sleeve in accordance with an exemplary embodiment of the present invention.

FIG. 15 is a cross section view of the sleeve and bone screw of FIG. 14.

FIG. 16 is a perspective view of the sleeve and bone screw of FIGS. 14 and 15 shown with the bone screw recessed within the sleeve in accordance with an exemplary embodiment of the present invention.

FIG. 17 is a cross section view of the bone screw recessed within the sleeve of FIG. 16.

DETAILED DESCRIPTION

The present invention is described herein and includes various exemplary embodiments in sufficient detail to enable those skilled in the art to practice the invention, and it should be understood that other embodiments may be realized without departing from the spirit and scope of the invention. Thus, the following detailed description is presented for purposes of illustration only, and not of limitation, and the scope of the invention is defined solely by the appended claims. The particular implementations shown and described herein are illustrative of the invention and its best mode and are not intended to otherwise limit the scope of the present invention in any way.

In general, the present invention facilitates the change in distance between objects, object portions, or surfaces, compresses objects or object portions together, and/or provides a configurable or random amount of pressure between surfaces. The system may facilitate changing, maintaining, reducing and/or expanding the distance between objects or object portions. The applied pressure may be suitably configured to be constant, increasing, decreasing, variable, random, and/or the like. In an exemplary embodiment, the invention includes a device which may be fixedly or removably attached to pathology, such as to a certain portion of a bone. In a particular embodiment, the device is fixedly or removably attached to the far cortex of the bone. In another embodiment, the invention includes a device or method for retracting the attached device to reduce the distance between the surfaces of the pathology. In a further embodiment, the invention includes a device and/or method for maintaining the pressure between the surfaces of pathology.

In an exemplary embodiment, and as shown in FIGS. 1 and 2, the lagwire system 1 includes a head or anchor component 2, a wire 12 and a cap 20. The lagwire system 1 may be fabricated using any type, amount or combination of materials suitably configured for the particular application. In an exemplary embodiment for medical applications, the lagwire system 1 is fabricated with stainless steel, titanium and/or titanium alloy which minimize reactivity with the body. Each component may be fabricated with various diameters, thread pitches, lengths and/or the like. The anchor component 2 may include threads, fins, tines, or any other fixation device or structure capable of securing the anchor component 2 to an object. Wire 12 may form any cross-sectional shape, width, thickness, diameter, and surface features along its length, and thus, for example, may form a simple cylinder and/or may include ribs, threads, serrations, one or more flat surfaces, bumps, and/or roughened surfaces along its length.

Figure 1A:
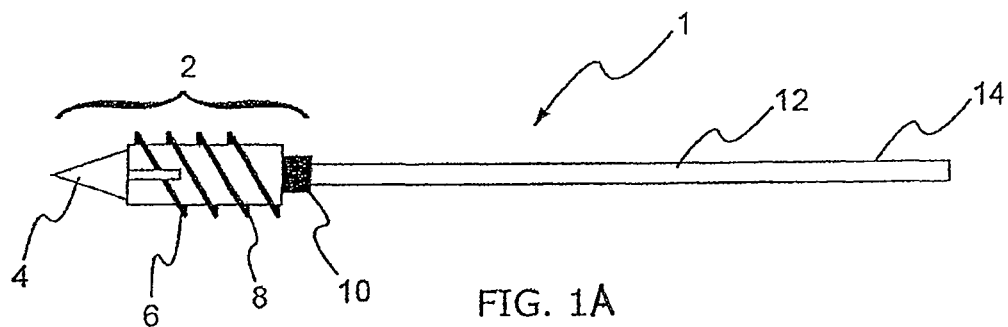
FIG. 1A is a lagwire system including a anchor component and wire in accordance with an exemplary embodiment of the present invention.

Certain exemplary components of the system will now be discussed. The anchor component 2 is any device which is configured to fixedly or removably attach to any object, such as pathology. In a particular embodiment, the anchor component 2 is configured to be fixedly or removably attached to the far cortex of the bone, as shown in FIGS. 4A-4G. As best shown in FIG. 1A, the anchor component 2 may include, for example, a self drilling tip 4 device which is suitably configured to puncture a hole and/or guide the anchor component 2, self cutting threads 6 which are suitably configured to cut thread grooves into the inside surface of a hole, fastening threads 8 which are suitably configured to mate with the newly formed thread grooves, and a tool attachment 10 suitably configured for mating with a tool head (e.g., hex head wrench, socket wrench, Phillips screwdriver, flathead screwdriver, allen wrench and/or the like).

Anchor component 2 may include different and interchangeable thread configurations, lengths, diameters, pitches and the like to facilitate insertion into different types of bone or other structures (e.g., cortical bone, cancellous bone, etc). Similarly, cap 20 may include different thread configurations, lengths, diameters, pitches and the like to facilitate insertion into different types of bone or other structures. For example, both the anchor component 2 and/or cap 20, may be interchangeably removed and replaced by different anchor components 2 and caps 20 with different thread configurations. Alternatively, the anchor component 2 may not be removable from the remainder of the wire 12.

Figure 1B:
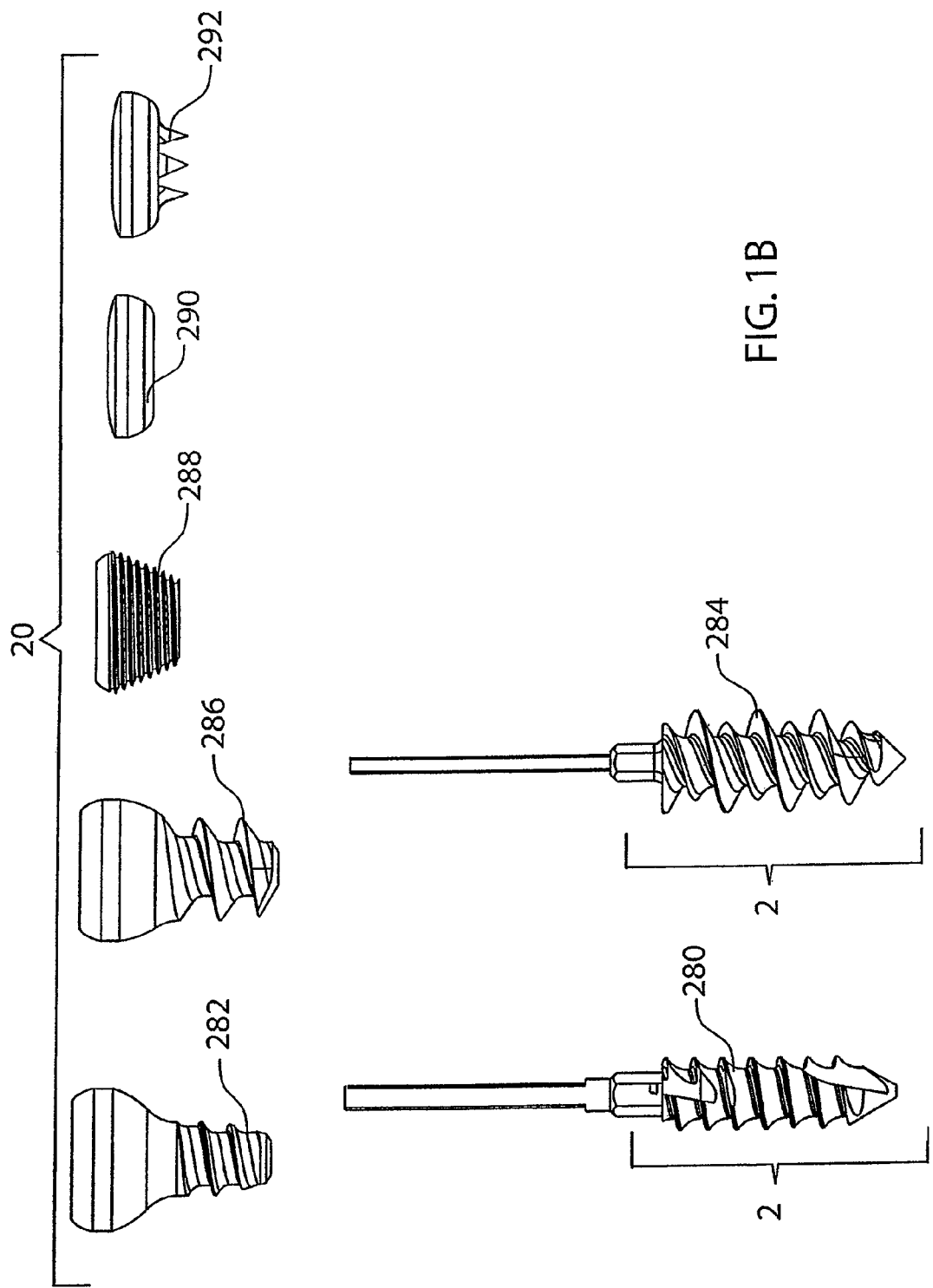
FIG. 1B is a lagwire system illustrating various thread combinations as embodiments of the present invention.

Examples of such thread configurations are illustrated in FIG. 1B and may be adapted for insertion into various bone or other structures. In one embodiment, the anchor component 2 includes leading threads 280 accommodating insertion into cortical bone while the cap 20 includes trailing threads 282 accommodating insertion into cortical bone. In another embodiment, the anchor component 2 includes leading threads 284 accommodating insertion into cancellous bone while the cap 20 includes trailing threads 286 accommodating insertion into cancellous bone. In another embodiment, the anchor component 2 includes leading threads 280 accommodating insertion into cortical bone while the cap 20 includes trailing threads 286 accommodating insertion into cancellous bone. In another embodiment, the anchor component 2 includes leading threads 284 accommodating insertion into cancellous bone while the cap 20 includes trailing threads 282 accommodating insertion into cortical bone. In another embodiment, the anchor component 2 includes leading threads 280 accommodating insertion into cortical bone while the cap 20 includes trailing threads 288 accommodating insertion a mechanical component such as a plate anchored into bone. In another embodiment, the anchor component 2 includes leading threads 284 accommodating insertion into cancellous bone while the cap 20 includes trailing threads 288 accommodating insertion a mechanical component such as a plate anchored into bone. In another embodiment, the anchor component 2 includes leading threads 280 accommodating insertion into cortical bone while the cap 20 includes a low-profile button-like design 290 that butts against the bone or a mechanical component. In another embodiment, the anchor component 2 includes leading threads 284 accommodating insertion into cancellous bone while the cap 20 includes a low-profile button-like design 290 that butts against the bone or a mechanical component. In another embodiment, the anchor component 2 includes leading threads 280 accommodating insertion into cortical bone while the cap 20 includes a low-profile button-like design that butts against the bone or a mechanical component and may also include spikes or teeth 292 to prevent rotation of the cap 20. In another embodiment, the anchor component 2 includes leading threads 284 accommodating insertion into cancellous bone while the cap 20 includes a low-profile button-like design that butts against the bone or a mechanical component and may also include spikes or teeth 292 to prevent rotation of the cap 20.

In another embodiment of a system 1, the cap 20 may be placed at both ends of the wire 12, and any combination of caps 20 threads or additional features may be used as preferred by an operator of the system 1. For example, in one embodiment, a first cap 20 includes cortical threads 282, cancellous threads 286, machine threads 288 accommodating insertion a mechanical component such as a plate anchored into bone, a low-profile button-like design 290 that butts against the bone or a mechanical component, and/or spikes or teeth 292 to prevent rotation of the first cap 20; and a second cap 20 includes cortical threads 282, cancellous threads 286, machine threads 288 accommodating insertion a mechanical component such as a plate anchored into bone, a low-profile button-like design 290 that butts against the bone or a mechanical component, and/or spikes or teeth 292 to prevent rotation of the second cap 20.

In a particular embodiment, the tip is on the front end of anchor component 2, followed by the cutting threads 6, the fastening threads 8, the tool attachment 10, then wire 12. The elements of anchor component 2 may be fabricated as one component or one or more elements may be configured to be removably or fixedly mated together to form anchor component 2. If mated together, a particular element may be exchanged for different applications. For example, if anchor component 2 needs to be inserted into a dense or hard bone, a stronger or sharper tip 4 may be screwed into thread element 6,8. Moreover, if deeper thread grooves are desired, cutting threads 6 may be replaced with greater diameter threads. Furthermore, if a different tool head is incorporated into a drill, tool attachment 10 may be exchanged with the appropriate attachment.

In one embodiment, the outside diameter of the fastening threads are similar to the thread diameters of known surgical screw sizes. Exemplary outside diameters of cortical anchor components include 3.5 mm and 4.5 mm, wherein the length of the thread section is similar to the cortex thickness. Exemplary outside diameters of cancellous (i.e., little or no cortex) anchor components include about 4.0 mm and 6.5 mm, wherein the length of the thread section may be about 16 mm or 32 mm.

Wire 12 is any device suitably configured, when force is applied, to reduce the distance between two surfaces. In one embodiment, wire 12 is configured to retract the anchor component 2 device to reduce the distance between the surfaces of the pathology. In one embodiment, anchor component 2 and wire 12 are constructed as one component. In another embodiment, anchor component 2 and wire 12 are constructed as separate components, but the components are configured such that the anchor component 2 may be threaded onto wire 12 after wire 12 is placed into the bone. Wire 12 further includes an interface component 14 on at least a portion of its surface, wherein the interface component 14 is suitably configured to limit the movement of cap 20 to move distally toward anchor component 2, but not proximally (backwards).

In an exemplary embodiment, interface component 14 of wire 12 includes a sawtooth like configuration such that one side of each tooth (e.g. the side closest to anchor component 2) is substantially perpendicular to the surface of wire 12, while the other side of the sawtooth is at a suitable angle, such as 45 degrees, thereby forming a triangular pattern for each sawtooth. In this manner, the inverse sawtooth on the inside surface of the cap slides or bends over the angled side of the wire sawtooth, but the substantially perpendicular side of the wire sawtooth restricts or limits the cap sawtooth from backwards movement. In another embodiment, any portion or the entire length of wire 12 includes any configuration such as, for example, round, oval, flat on one or more portions of the wire, and/or microgrooves or ridges along the wire (which may include the sawtooth configuration, indentions or other configurations) to increase the friction along the wire. In one embodiment, wire 12 holds 20 pounds of pull; however, microgrooves in the wire may significantly increase the strength of the wire 12.

In an exemplary embodiment, wire 12 is comprised of a thin metal such as, for example, stainless steel, titanium and/or titanium alloy, so it may be easily cut to almost any desired length, thereby eliminating or reducing the need for fixed lengths screws. As such, the invention substantially reduces or eliminates the need for the inventory or availability of large screw sets or multiple screws. Moreover, because the system may include numerous materials, configurations and designs for either wire 12 or cap 20, the invention provides increased versatility because the physician is provided with multiple options and choices for wire 12 and cap 20 combinations.

Figure 2A:
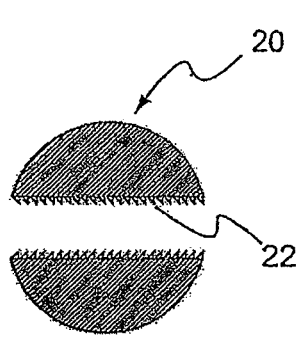
FIG. 2A is a quick cap in accordance with an exemplary embodiment of the present invention.
Figure 2B:
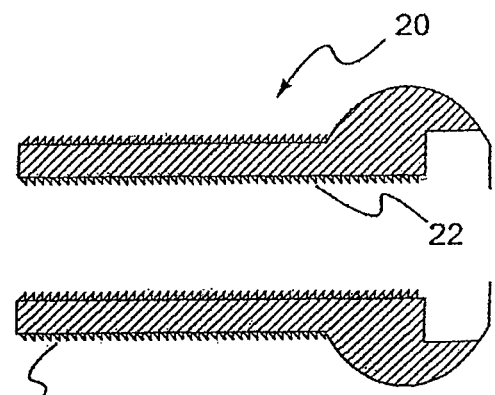
FIG. 2B is an alternative embodiment of a quick cap in accordance with an exemplary embodiment of the present invention.
Figure 2C:
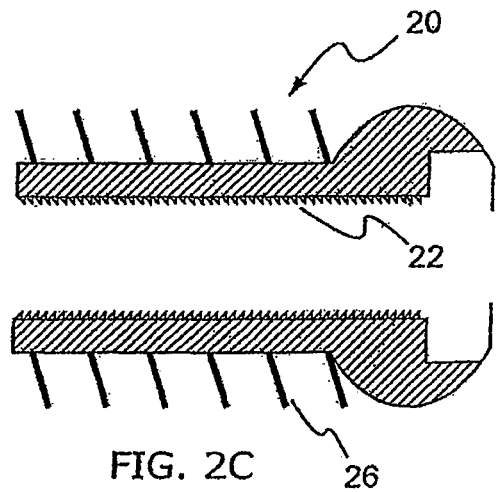
FIG. 2C is a screw cap in accordance with an exemplary embodiment of the present invention.
Figure 2D:
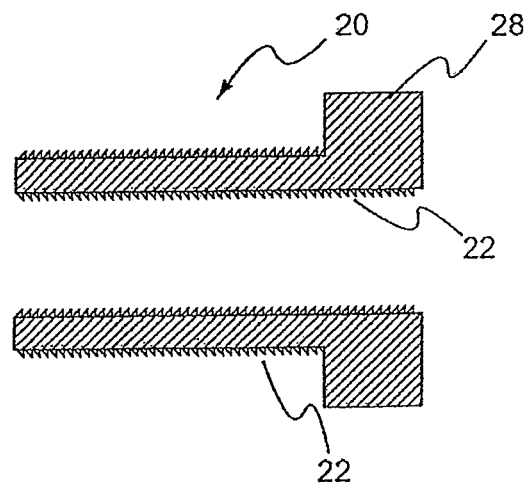
FIG. 2D is a flat cap in accordance with an exemplary embodiment of the present invention.

Cap 20 is any device suitably configured to maintain or increase the pressure between the surfaces of pathology by limiting wire 12 movement. As shown in FIGS. 2A-2E, exemplary caps 20 may include various configurations, materials, shapes and/or sizes. In one embodiment, and as shown in FIG. 2A, cap 20 includes an inverse interface component 22 relative to wire 12 interface component such that cap 20 is restricted from backwards translation after cap 20 is inserted over wire 12. In one embodiment, the interface component 22 on cap 20 is located at least on the inside surface of the cap and includes a saw tooth pattern with the same or similar pitch as the saw tooth on wire 12. This configuration also allows cap 20 to slide along wire 12 without the need for spinning cap 20 which is important because time is of the essence in a medical procedure and spinning the cap down a sufficiently long length of wire would be very time-consuming. Examples of cap 20 include a screw cap 20, flat cap 20 and a quick cap 20. As shown in FIG. 2C, screw cap 20 is configured with teeth 22, cutting threads 24 and/or mating threads 26 on the outside surface to facilitate rotating cap 20 into the cortex to, for example, fix surgical plates against certain pathology. However, cutting threads 24 may not be needed on any of the caps because cutting threads 6 of anchor component 2 may have already tapped the threads on the inside surface of the bone, so the teeth 22 or mating threads 26 alone can simply rotatably engage the threads formed from cutting threads 6 and provide sufficient friction to secure the cap in the bone. As shown in FIG. 2D, flat cap 20 may include teeth 22, cutting threads 24 and/or mating threads 26 on the outside surface to facilitate rotating cap 20 into the cortex, but it also is configured with a flat top surface 28 to allow cap 20 to be inserted into the cortex such that the flat top surface 28 of cap 20 does not substantially protrude from the cortex surface. As best shown in FIG. 2A, for example, the quick cap 20 or any other cap may be configured with only the interface component on the inside surface, thereby allowing for quick and easy assembly.

Figure 2E:
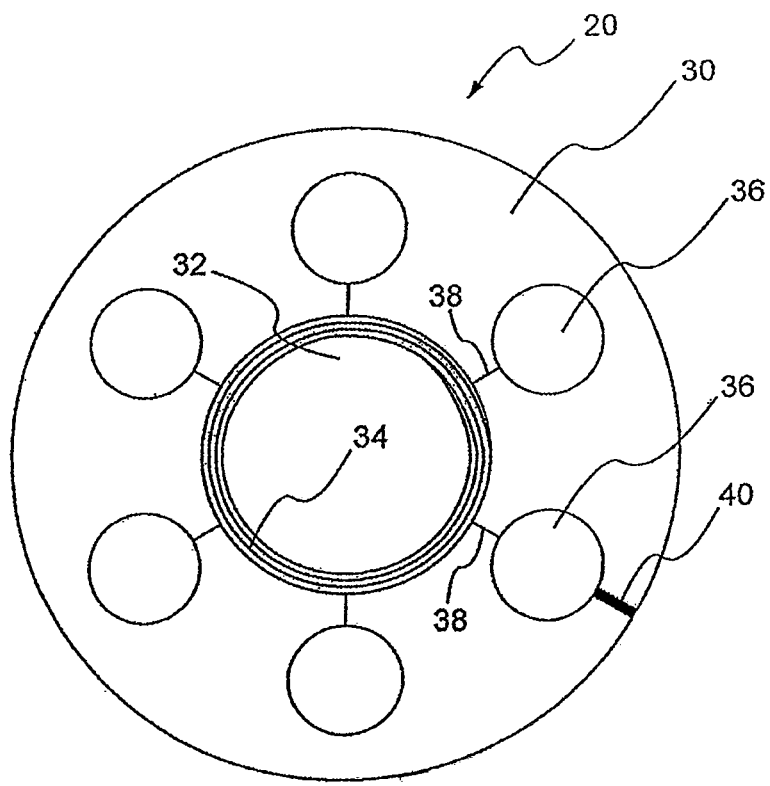
FIG. 2E is a top view of an alternative embodiment of a cap in accordance with an exemplary embodiment of the present invention.

With reference to FIG. 2E, in one embodiment, cap 20 is configured as a planar disk 30 with a center hole 32, wherein the center hole 32 includes an interface component 34 on its inner circumference surface. In an exemplary embodiment, the pitch of the saw tooth interface component is about 0.25 mm-0.5 mm. The planar disk 30 may also include any configuration for facilitating expansion of the disk 36 while sliding down wire 12. The configurations may include, for example, a cut 38 or a hole 36 in the planar disk 30. The planar disk may include multiple holes or cuts spaced over the planar surface. One or more of the additional holes 36 may also be connected to a cut 38 in the planar surface that extends to the center hole 32. One or more of the holes 36 may also be connected to a cut 40 in the planar surface that extends to the outside edge of the planar surface. In one embodiment, six additional holes 36 are evenly spaced around the planar surface with each hole 36 connected to a cut 38 which extends to the center hole, while one hole 36 also includes a cut 40 that extends to the outside edge of the planar surface.

The planar disk may also set inside a shallow cup device, wherein the circumference of the cup is slightly larger than the circumference of the planar ring in order to allow expansion of the ring. Moreover, a spring, or any other device suitably configured to apply pressure to cap 20, is placed between the planar ring and the cup device. In one embodiment, a bellville spring is used to apply pressure to the cap 20. The spring is configured to provide force on wire 12 after resorption. During the healing process, cartilage forms at the fracture and the cartilage compresses, so bone resorption typically occurs at the location of the fracture. When force on the lagwire is released due to bone resorption during healing, in one embodiment, cap 20 allows for auto tightening of the lagwire because micro-motions or vibrations will often cause cap interface device 22 to click down another notch on the inverse interface device of the wire 12.

Figure 2F:
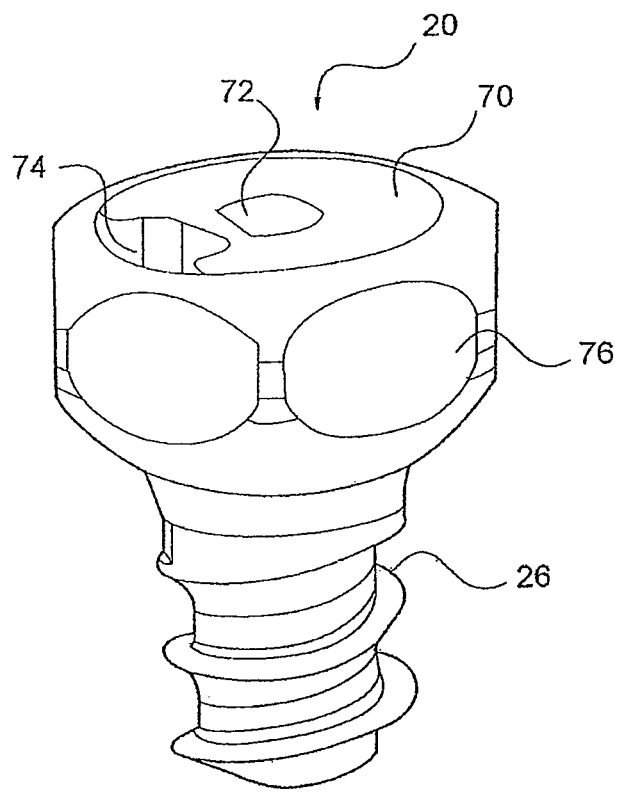
FIG. 2F is a perspective view of another embodiment of a cap in accordance with an exemplary embodiment of the present invention.
Figure 2G:
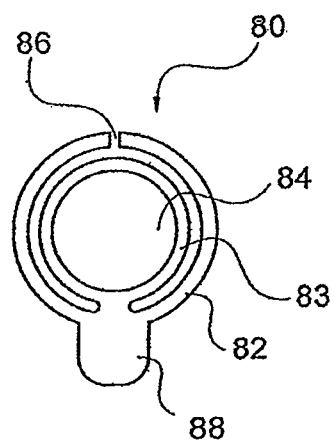
FIG. 2G is a top view of an exemplary spring in accordance with an exemplary embodiment of the present invention.

Another embodiment of a cap 20 is shown in FIG. 2F. As discussed above, cap 20 fits over one end of wire 12, such that cap 20 permits travel of cap 20 in one direction (e.g., distal travel with respect to the wire, toward the bone), but resists travel of cap 20 in the other direction (e.g., proximal travel with respect to the wire, away from the bone). In exemplary embodiments, cap 20 includes cutting threads 26, cover 70, a spring 80 and substantially flat surfaces 76 around the circumference of cap 20 to facilitate griping and/or turning cap 20. Cap 20 may be configured with a wider upper section which includes flat surfaces 76 around its circumference, and a tapered lower section with a gradually reducing diameter. Cutting threads 26 extend from the lower section. Cap 20 may include different thread configurations, lengths, diameters, pitches and the like to facilitate insertion into different types of bone or other structures (e.g., cortical bone, cancellous bone, etc).

Cover 70 may be integral with cap 20, or may be a separate component which is permanently or temporarily set in, or affixed to, cap 20. In one embodiment, cover 70 includes an opening 72 (e.g., in center of cover 70) which receives wire 12 and an inlet 74 which is configured to receive a component of extractor tool 90.

In one embodiment, tension spring 80 is set inside cap 20. In one embodiment, and with reference to FIG. 2G, tension spring 20 sits within cap 20 below cover 70; is circular; includes opening 84 (e.g., in center of circular ring) which receives wire 12; includes an outer ring 82 and an inner ring 83; includes a cut into, or non-connecting portion 86 of, outer ring 82 and/or inner ring 83; and/or includes a tab 88 which extends outward from outer ring 82. Outer ring 82 and an inner ring 83 may be one integrated ring, or two or more separate rings, which may not be connected, or may be connected in any manner.

At least a portion of inner ring 83 (or any portion of inner circumference of tension spring 80) provides greater friction against wire 12 one way (e.g., when the cap is pulled proximal, away from the bone). The friction is asserted against wire 12 because cover 70 impacts tab 88, so tab 88 forces tension spring 80 to flex, torque and/or tilt (e.g., 15 degrees) opening 84, thereby causing at least a portion of inner ring 83 to assert friction against at least a portion of wire 12. When cap 20 is pushed the other way (e.g., when the cap is pushed distal, toward the bone, using extractor 90), tab 88 is forced away from cover 70 and does not tilt, so it does not engage any surface, and the wire is able to translate, with minimal or no friction, through the central opening in the tension spring.

Another embodiment of a cap 20 is shown in FIGS. 2H, 2I, and 2J. FIG. 2H shows and exploded view of an example of the cap 20 with a cover or recessed nut 70, an angle or lever clutch 300, a tension spring 80, and a body 302. When assembled, as shown in the perspective view of FIG. 2I or cross section view of 2J, the tension spring 80 resides within a chamber of the body 302, between the body 302 and the cover 70. The locking lever clutch 70 also resides between the body 302 and the cover 70, and is in movable contact with the spring 80. The spring 80 is a flat spring washer that applies a preloaded force to the lever clutch 300, biasing the lever clutch 300 to skew to a plane that is not parallel with the plane of the spring 80. In its skewed state, the lever clutch 300 includes defines a hole 304 along a central axis 306 that is not coaxial with a central axis 308 of the cap 20, and frictional edges 310 defining a portion of the hole 304 are forced into frictional contact with one or more flat or rounded outer surfaces of a wire 12 running along the axis 308 of the cap.

The tension spring 80 may, for example, be formed of a relatively thin layer of nitinol or another resilient material. The lever clutch 300 may, for example, be formed of a thicker layer of stainless steel or titanium. The relatively thin layer of the tension spring 80 occupies minimal space within the chamber of the body 302, minimizing the overall size of the cap 20. The relatively thick layer of the lever clutch 300 provides greater surface area and strength to maximize stable and strong frictional contact and lock between the frictional edges 310 and the outer surface of the wire 12. In an exemplary embodiment, the lever clutch 300 and spring 80 are either attached to each other or formed as a single structure and may be formed of identical or varying materials and thicknesses.

The frictional edges 310 permit distal movement of the cap 20 with respect to the wire 12 as the wire 12 moves through the central axis 308 of the cap 20 and forces or biases the locking lever clutch 300 to move upwards towards the cover 70, towards a plane that is closer to parallel with the plane of the spring 80, and in an orientation that permits the body of the wire 12 to move through the hole 304 with less frictional contact against the frictional edges 310. In contrast, the frictional edges 310 resist proximal movement of the cap 20 with respect to the wire 12 as the wire 12 moves through the central axis 308 of the cap 20 and forces or biases the locking lever clutch 300 to move downwards away from the cover 70, towards a plane that is closer to perpendicular with the plane of the spring 80, and in an orientation that resists movement of the body of the wire 12 through the hole 304 as the frictional edges 310 are forced against and in increasing frictional contact with the outer surface of the body of the wire 12.

The embodiment of a cap 20 described with reference to FIGS. 2H, 2I, and 2J can be unlocked during or after initial implantation to make adjustments to, replace, or remove any or all of the system 1. To unlock the lever clutch 300 of the cap 20, a user may manually, or by means of a special hook-like tool, raise a handle 312 of the clutch 300, for example, by exerting force on a lower edge 314 of the handle 312 in a direction that releases the friction edges 310 from their locking position with respect to the outer surface of the wire 12.

Figure 5A:
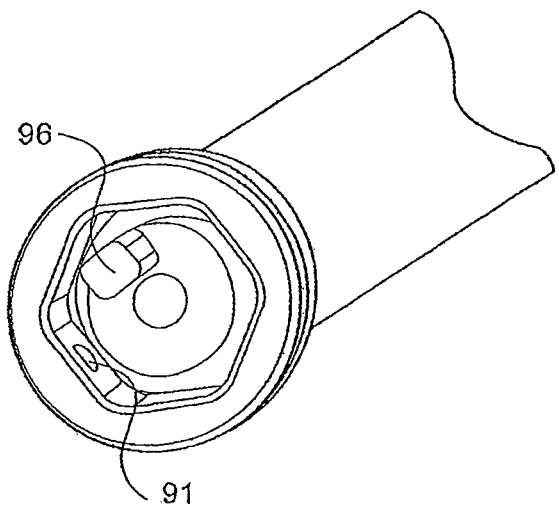
FIG. 5A is an exemplary head of the extractor of FIG. 5B in accordance with an exemplary embodiment of the present invention.
Figure 5B:
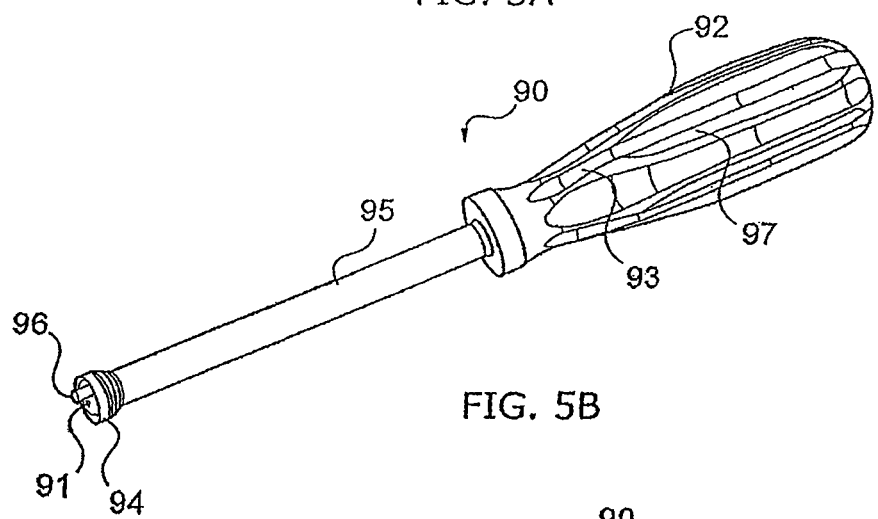
FIG. 5B is an exemplary extractor in accordance with an exemplary embodiment of the present invention.

Extractor/Driver 90, with reference to FIGS. 5A and 5B, includes any device suitably configured to insert and/or extract cap 20. In one embodiment, extractor 90 includes one or more ball bearings 91, shaft 95, shaft end 93, handle 92 which receives shaft end 93, tip sleeve 94, tip 96, and/or spring 97. Tip 96 may be the end of a long rod which extends upward into handle 92. Spring 97 applies pressure against the upper end of the rod that emanates from tip 96, thereby asserting a load against tip 96. Tip 96 is thus configured to be received into inlet 74 of cap 20 and the spring-load maintains tip 96 in inlet 74. Tip sleeve 94 is configured to receive cap 20 to also facilitate rotation and/or translation of cap 20. Tip 96 is mounted on a disc such that it allows tip sleeve 94 to more fully receive cap 20. The disc also rotates such that extractor 90 may rotate around cap 20, with minimal or no movement of tip 96. Ball bearings 91 are configured to facilitate rotation of tip sleeve 94 around outer surface of cap 20.

Figure 5C:
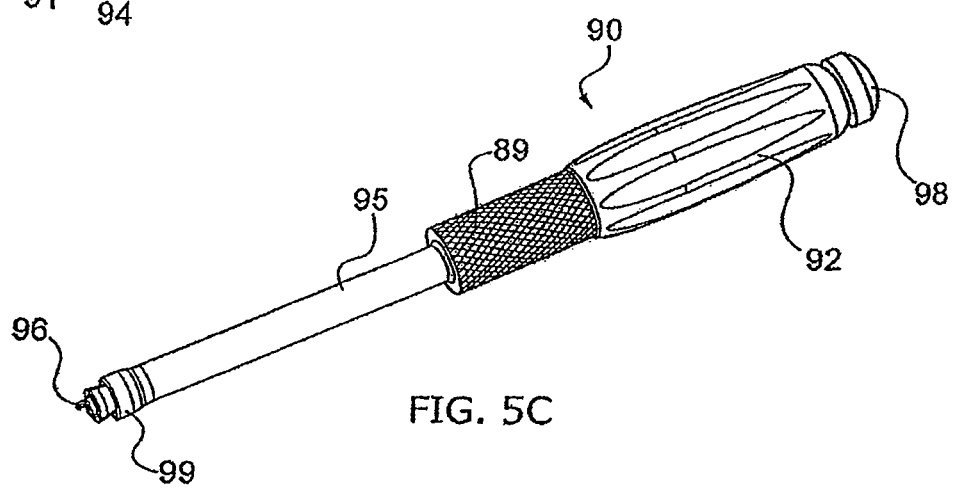
FIG. 5C is another embodiment of an exemplary extractor in accordance with an exemplary embodiment of the present invention.

Another embodiment of extractor/driver 90 is shown in FIG. 5C. In this alternative embodiment, the rod may have a first end which includes tip 96, and a second end 98 which may exit handle 92 such that the user may apply pressure to the second end 98 of the rod, thereby similarly applying pressure and a load against tip 96. Exit handle 92 also rotates such that it enables rotation of tip 96 which allows the user to rotate tip 96 until tip 96 mates with the inlet in cap 20. In another embodiment, collet sleeve 99 is attached to collet advancing handle 89. Collet advancing handle 89 includes a threaded inner surface which is configured to advance shaft 95, and thus, advance collet sleeve 99 forward over cap 20 to facilitate grasping of cap 20 for removal of cap 20.

Figure 3A:
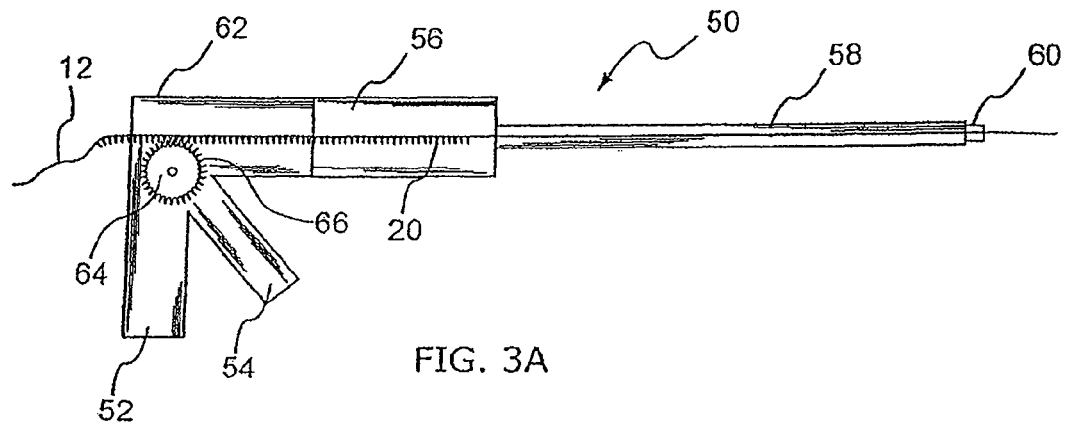
FIG. 3A is a tensioner in accordance with an exemplary embodiment of the present invention.

A tensioner 50 may also be used in conjunction with the present invention. With respect to FIG. 3A, tensioner 50 is any device suitably configured to insert a cap 20 into an object and/or provide tension to a wire 12. In one embodiment, tensioner 50 increases the pressure between the surfaces of pathology by providing force to a wire 12 while the anchor component 2 of wire 12 is fixed into a bone or far cortex. In an exemplary embodiment, tensioner 50 includes a handle 52 with a hand trigger 54, wherein the handle 52 supports a rotatable barrel 56 which mates with a cylindrical rod 58. Cylindrical rod 58 may be cannulated to receive wire 12 and/or have a driver 60 (e.g., hex, phillips, screw, allen and/or the like) at its distal end for mating with the tool attachment 10 of anchor component 2. The barrel 56 may be rotated manually or automatically in order to rotate the driver 60 into the object (e.g., bone or cortex). In one embodiment, tensioner 50 includes a means for exerting a force on wire 12, such as, for example, internal gears 64, wherein the gears 64 include an interface component 66 (e.g., saw tooth) which mate with the inverse sawtooth 20 on wire 12. By pivoting the hand trigger 54, the internal gears are rotated such that the gears cause wire 12 to translate out the back end 62 of the tensioner 50, thereby exerting force on wire 12 which is fixed at its distal end. The tensioner 50 may also include a gauge type device or any other device which is suitably configured to measure and/or display the tension exerted on wire 12.

Figure 3B:
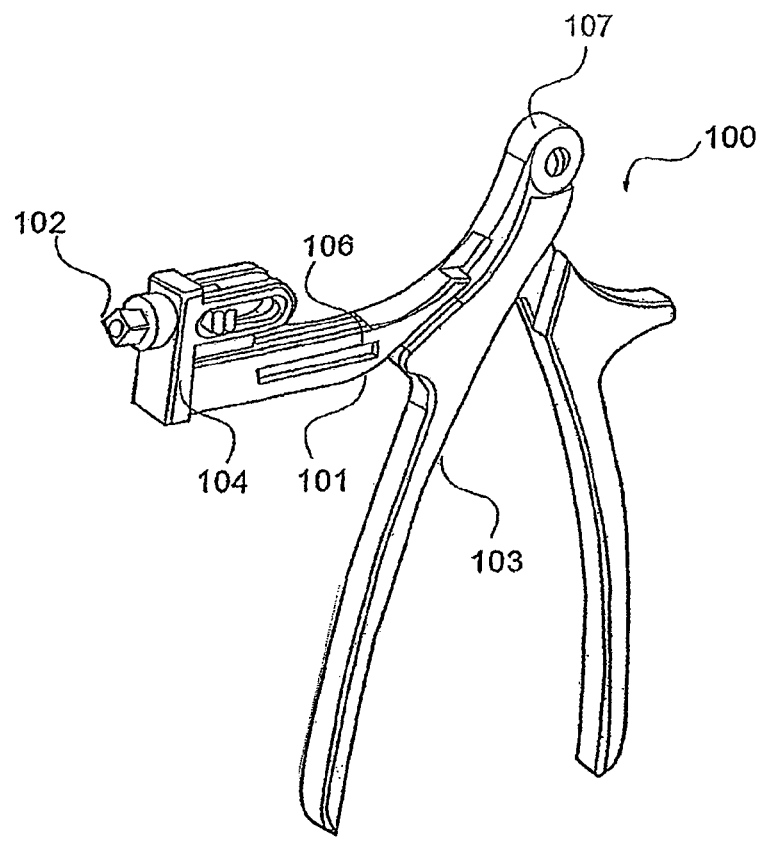
FIG. 3B is another embodiment of a tensioner in accordance with an exemplary embodiment of the present invention.

Another embodiment of a tensioner (e.g., tensioner 101) is shown in FIG. 3B. In one embodiment, tensioner 100 includes a base 101, a DVR connect component 102, a handle 103, a lock 104, and/or a spring link 106. Tensioner 100 is configured to accept multiple size wires and may include an indicator to show the amount of tension being applied. Tensioner 101 is also configured such that extractor 90 may clip into tensioner 101.

Figure 6:
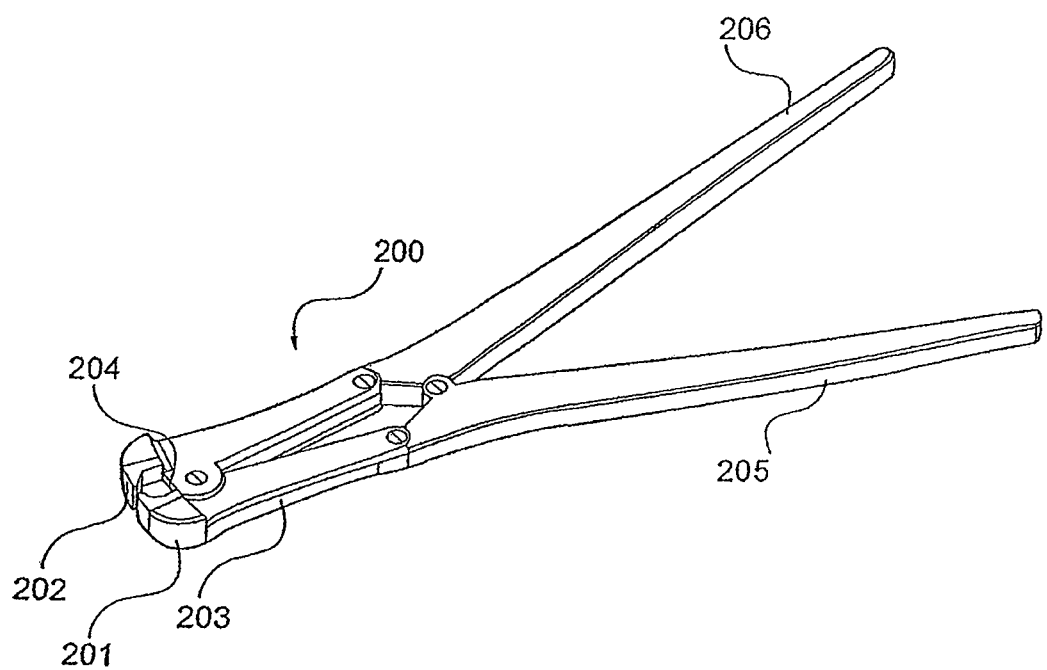
FIG. 6 is an exemplary cutter in accordance with an exemplary embodiment of the present invention.

After tensioning wire 12 to the desired tension, wire 12 may be cut, broken or shortened using any known device or method. With reference to FIG. 6, cutter 200 may be used. Cutter 200, in one embodiment, includes insert left 201, insert right 202, jaw left 203, jaw right 204, cutter left 205, and cutter right 206. Cutter 200 includes a cutting surface that extends beyond the main body of cutter 200 such that the wire may be cut from various angles.

The various components discussed herein can be suitably configured to perform the following method, wherein the steps can be performed in any order and any individual step is not necessary to the method. In an exemplary embodiment, a cannulated lagwire driver is suitably attached to a surgical drill, such that the drill allows for automatic rotation of the driver. The wire 12 of lagwire system 1 is placed into the channel of the driver such that the end of the driver encompasses or is received into driver head 10 of anchor component 2, thereby allowing wire 12 to be drilled into the bone. In one embodiment, anchor component 2 is configured with a hex head as the driver head 10 such that the driver suitably mates to the hex head. The anchor component 2 and wire 12 are then drilled into the bone to a desired depth using the automatic surgical drill (or any other manual or automatic device for rotating anchor component 2). Specifically, drill tip 4 of anchor component 2 facilitates the drilling of a pilot hole, wherein the proximal cutting threads 6 tap the bone for threading the inner surface of the hole, then the proximal mating threads 8 rotationally mate with the newly created threaded surface, thereby temporarily attaching the anchor component 2 into the cortex of the bone.

After attaching the anchor component 2 to the bone, the surgical drill is removed and a cap 20 is threaded onto the proximal end 14 of wire 12. Cap 20 is then translated distally along wire 12 until cap 20 contacts the bone or other desired pathology. In one embodiment, a lagwire tensioner is used to exert tension on the lagwire. In another embodiment, a lagwire tensioner 50 may be used to force or seat cap 20 into the bone surface or any other desired position. The hex head 60 of the tensioner 50 may be used to screw cap 20 into the bone surface. In another embodiment, the lagwire tensioner 50 exerts tension on the lagwire 12 up to a desired tension which may be read from a gauge communicating with the tensioner.

After positioning the lagwire device 1 and applying the appropriate amount of tension, in one embodiment, the excess wire 12 may be suitably removed by, for example, a wire cutter or any other suitable device. In another embodiment, a crimp type device may be placed on wire 12 to also help maintain tension. The crimp may include a clamp type device, bending the existing wire 12, screwing a nut onto the end of wire 12 and/or the like. The crimp may be placed on wire 12 after cap 20 is set in place, for example, in order to crimp other end pieces together. The tensioner 50 may also be used to reverse screw cap 20 in order to remove a wire 12 out of the bone. Moreover, in a situation where anchor component 2 strips out of the bone (for example, when the bone is of poor quality), the present invention allows the lagwire to be pushed through the opposite side of the bone and through the skin such that the anchor component 2 of wire 12 can be suitably removed (e.g., cut off) and a cap 20 can be placed onto that end of the lagwire, thereby resulting in better purchase (e.g., quality of fixation) of the bone.

Figure 4A:
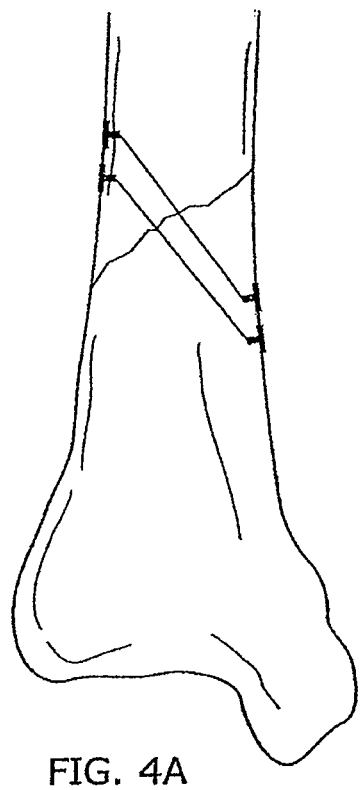
FIG. 4A is a fixation of a bone fracture in accordance with an exemplary embodiment of the present invention.
Figure 4B:
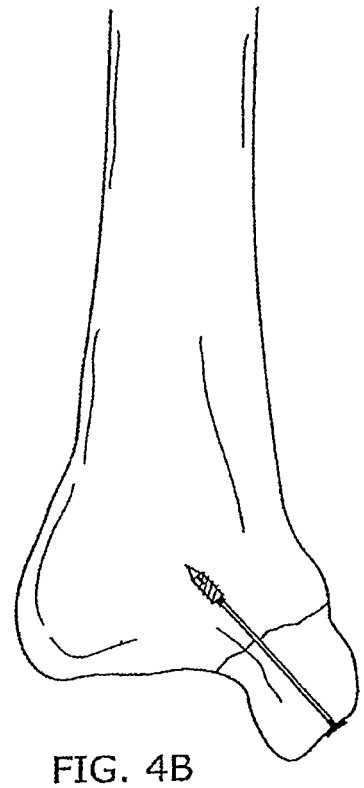
FIGS. 4B-4D are fixations of fractures of a certain portions of a bone in accordance with an exemplary embodiment of the present invention.
Figure 4C:
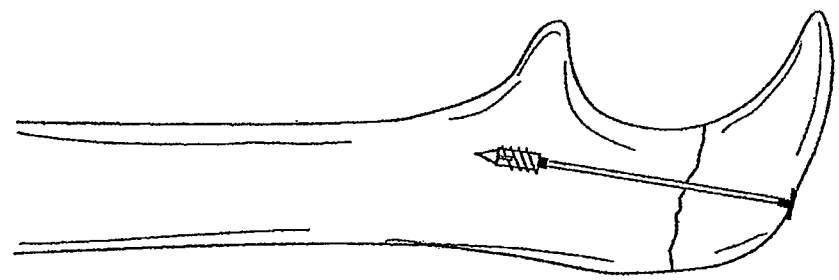
Figure 4D:
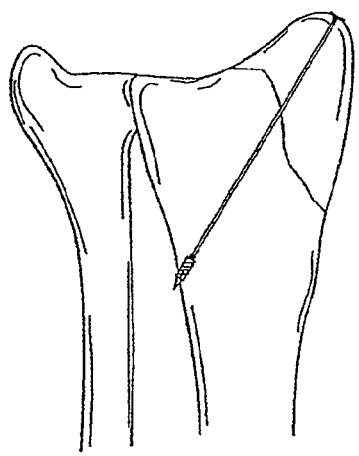
Figure 4E:
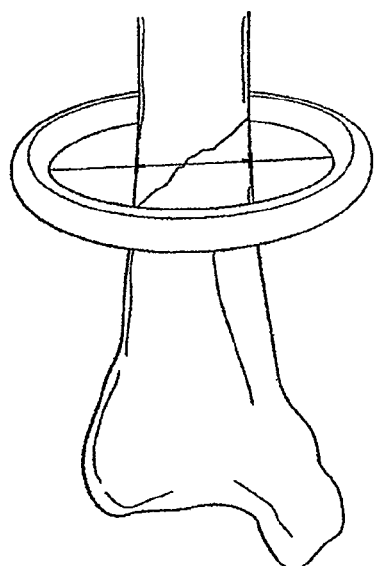
FIG. 4E is a fixation of a bone fracture by inserting the lagwire through the entire limb to facilitate attaching an external fixation device to the limb in accordance with an exemplary embodiment of the present invention.
Figure 4F:
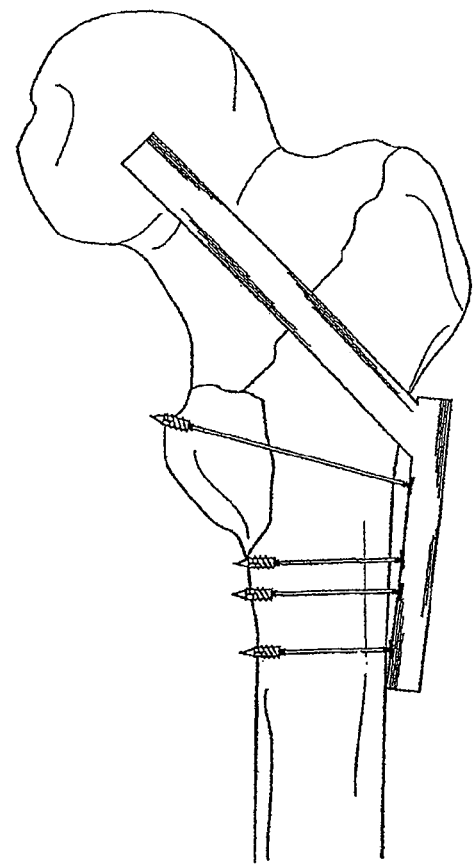
FIGS. 4F-4G is a fixation of a bone fracture by inserting the lagwire through the entire limb to facilitate holding a plate to the bone to help fix certain types of fractures in accordance with an exemplary embodiment of the present invention.
Figure 4G:
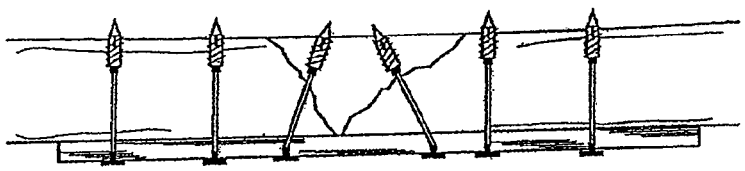

With respect to FIGS. 4A-4G, the lagwire system discussed herein can be used for the fixation of various types of bone fractures. FIG. 4A shows the use of the present invention for an exemplary fixation of a bone fracture or break. FIGS. 4B-4D show the use of the present invention for an exemplary fixation of fractures of certain portions of bones. Moreover, as shown in exemplary FIGS. 4F and 4G, the lagwire system 1 may also be used in a similar manner discussed herein in order to assist in holding a plate to the bone to help fix certain types of fractures. In other types of fractures, the lagwire may be placed through an entire limb to, for example, attach an external fixation device to the limb as shown in exemplary FIG. 4E.

Figure 4H:
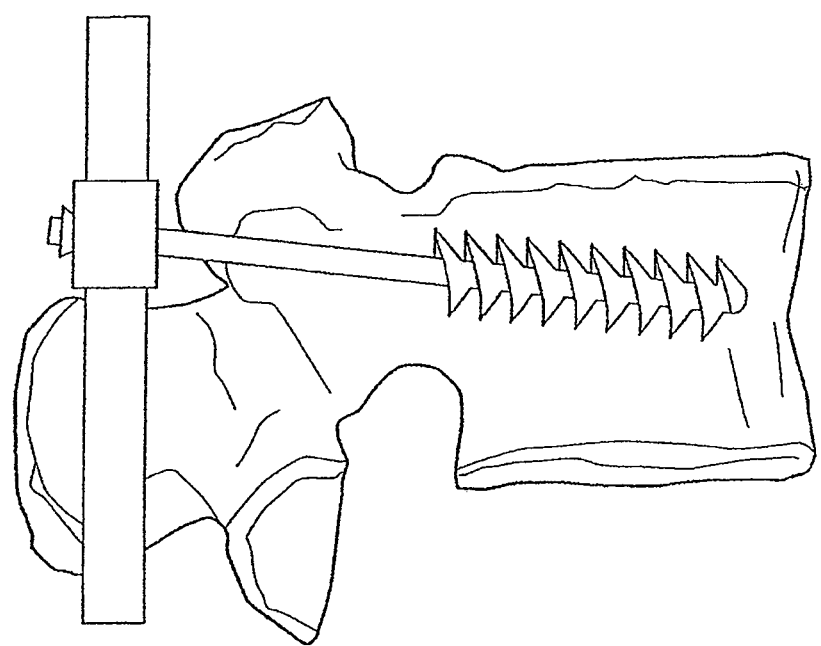
FIG. 4H is a fixation of a spinal injury in accordance with an exemplary embodiment of the present invention.

FIG. 4H shows a fixation of a vertebrae in accordance with an exemplary embodiment of the present invention. The screw is inserted into the vertebrae, then a cap is fitted onto the end of the wire. The cap is specially constructed such that the cap attaches to a rod. The rod may extend along various vertebrae such that the lagwires may extend from various vertebrae and all connect to the same rod. Another screw and lagwire may be inserted into the other side of the vertebrae such that the wire extends from the other side of the vertebrae and its cap connects to a second rod on the other side of the vertebrae for additional stability.

As described herein, the system and method of the present invention provides a device which is self-drilling, self-tapping and can be inserted under power. The invention also facilitates reducing and fixing fractures in one step. As such, the invention substantially expedites the process for fixation of bone fractures which is, of course, critical during trauma situations in order to stabilize a patient or to minimize the amount of time the patient is on the operating table or under anesthesia. In contrast to typical prior art screws wherein a gliding hole in the near cortex simply guides the screw, the present invention provides the ability for two sides of cortex bone screw fixation. Moreover, because of the strength of the attachment to the bone, the invention enables sufficient fixation even in poor quality bone material. Furthermore, wherein the prior art systems often require the use of cannulated screws in order to utilize a guidewire for placement, the present invention does not require the use of cannulated screws. Because the lagwire includes a tip 4 which creates a pilot hole, taps the bone for threads and fixes the threads into the bone, the system and method minimizes the possibility of inaccurate placement into the distal cortex or missing the distal hole.

In prior art systems, the physician typically cuts a relatively large opening in the skin in order to locate the bone segments, pull the bone segments into alignment, then place the screw into the bones. In the present invention, the system facilitates the percutaneous technique by allowing the physician to cut a minor incision into the skin for the anchor component, insert the anchor component, then pull the bones together with wire 12 and set the cap, all without large incisions or additional incisions.

Another embodiment for a bone fixation device includes a collapsing bone fixation device which is suitably configured to collapse in association with a fracture collapse to minimize or prevent the device from protruding beyond the bone. In an exemplary embodiment, the bone fixation device also includes an internal (i.e., minimal or no contact with the bone) compressive device 140 to maintain compression across the fracture during fracture collapse (e.g., weight bearing by the patient).

Figure 7:
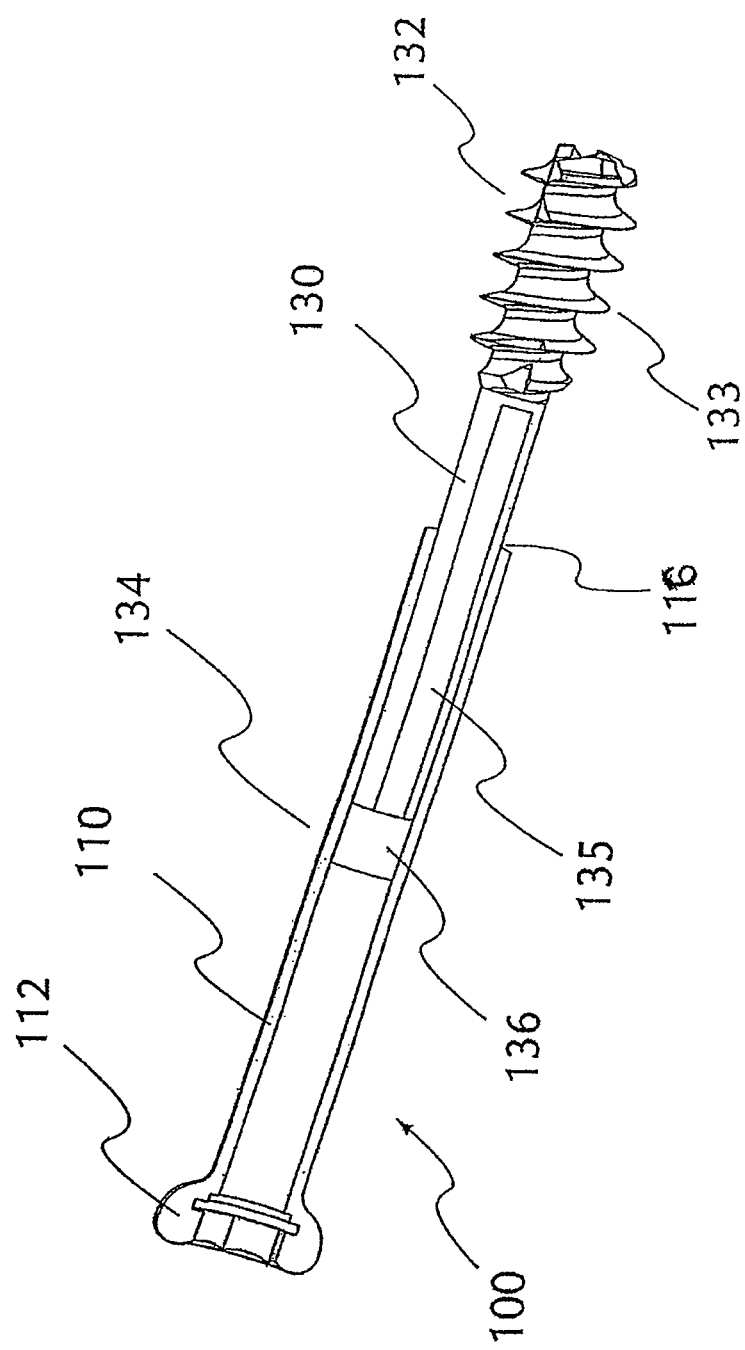
FIG. 7 is a cannulated screw having a sleeve and a threaded shaft in accordance with an exemplary embodiment of the present invention.

With respect to FIG. 7, an exemplary embodiment includes an improved screw 100 having a sleeve 110 and a shaft 130. In one embodiment, no additional elements exist between sleeve 110 and shaft 130, but in other embodiments (as discussed below in more detail and in FIGS. 8 and 9), a compressive device 140 (e.g. spring) is located between sleeve 110 and shaft 130. In an exemplary embodiment, each of the elements sleeve 110, shaft 130, and compressive device 140 are cannulated.

In one embodiment, with respect to FIG. 7, shaft 130 includes a first end 132 having a gripping device 133 and a second end 134. Gripping device 133 may include any structure and configuration for enabling shaft to enter and attach to an object. In one embodiment, gripping device includes a threaded surface thereon. The threaded surface may include cutting threads, mating threads, barbs, ribbed surface or any other surface configured to retain shaft 130 into an object. In an exemplary embodiment, gripping device 133 is about 0.63 inches in length with a pitch of about 9 threads per inch.

In one embodiment, shaft 130 is generally cylindrical, but includes one or more flat outer surfaces 135. In a particular embodiment, second end 134 includes two rectangular flat, opposing surfaces which extend over the entire length of shaft 130, but terminate prior to gripping device 133. In an exemplary embodiment, the flat surfaces of shaft 130 are each about 1.25 inches in length.

In one embodiment, second end 134 of shaft 130 is configured to restrict shaft 130 from translating beyond a particular location with respect to the sleeve 110. In an exemplary embodiment, end cap 136 is located on or near second end 134, and is formed in a cylindrical configuration such that end cap 136 freely translates within the cylindrical portion of sleeve 110, but end cap 136 stops the translation of shaft 130, when end cap 136 impacts the flat inner surface of sleeve 110. End cap 136 limits the expansion of compressive device 140 to a certain point, so continued compression can be applied against the fracture. End cap 136 may be integral with shaft 130, welded onto shaft 130, or otherwise affixed to shaft 130.

With continued reference to FIG. 7, a wider diameter head 112 is located at the first end of sleeve 110. An exemplary diameter of head 112 is about 0.387 inches. Head 112 includes a recessed portion for receiving the hex head of a tool. One skilled in the art will appreciate that head 112 may be any configuration suitably configured to receive any suitable working tool. The recessed portion is about 0.10 inches in depth and about 0.198 inches wide. Head 112 (or any other portion of sleeve 110) may also include a ledge 114 (FIG. 8) for retaining compressive device 140 within sleeve 110. Cap 20 (discussed above in other embodiments) may be configured as sleeve 110 (or barrel) and any components of cap 20 may be incorporated into bone screw 100.

A second end of sleeve 110 includes an opening 116 which receives shaft 130 such that shaft 130 is able to at least partially move within sleeve 110, with minimal or no movement of sleeve 110. As discussed above, in one embodiment, the inner surface of sleeve 110 is generally cylindrical, but the inside surface also includes two rectangular flat, opposing surfaces which extend along a portion of the length of sleeve 110. In an exemplary embodiment, the overall sleeve 110 is about 1.85 inches long, about 0.22 inches outer diameter, and about 0.161 inner diameter with a reduced distance between the flat surfaces of about 0.14 inches with the flat surfaces of sleeve 110 being each about 0.545 inches in length.

Figure 8:
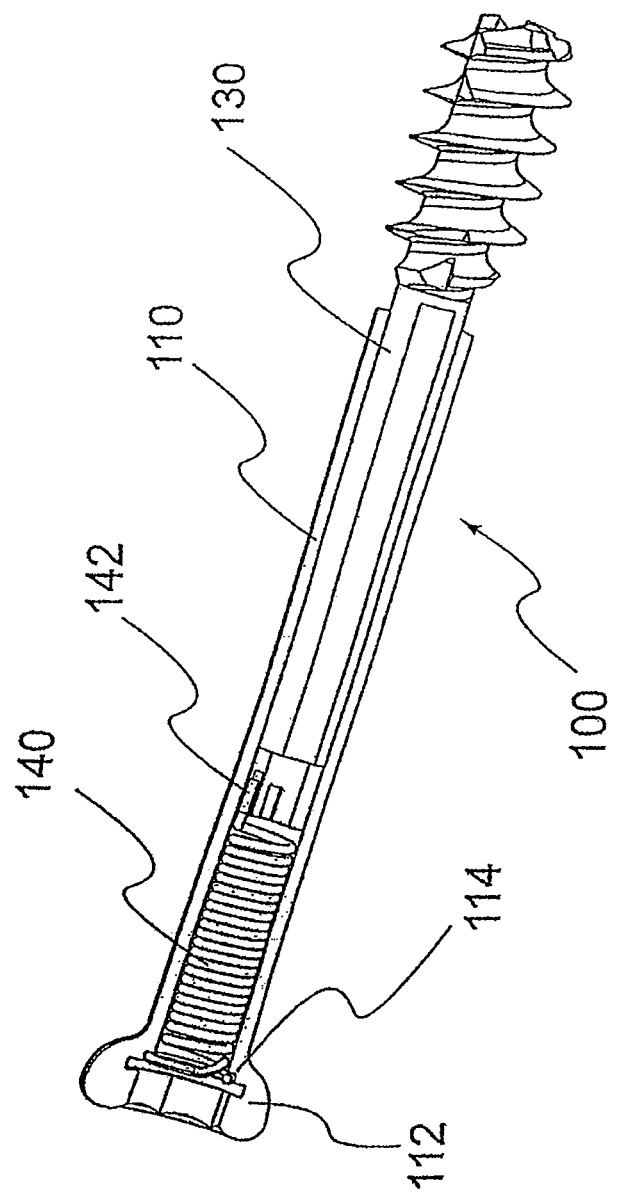
FIG. 8 is a cannulated screw having a sleeve, a compressive device and a threaded shaft and shown prior to extending the compressive device, in accordance with an exemplary embodiment of the present invention.

In one embodiment, and with respect to FIG. 8, a compressive device 140 exists between sleeve 110 and shaft 130 such that compressive device 140 exerts a force directly or indirectly against shaft 130. Compressive device 140 may include, for example, a spring or any other element which exerts a force and/or bears a load. In one embodiment, compressive device 140 is located inside sleeve 110 (as discussed above). In a particular embodiment, compressive device 140 is a spring having about 10 mm of extension. As such, compressive device 140 allows about 10 mm of compression before sleeve head 112 is no longer held against the cortex.

Compressive device 140 may be suitably affixed to sleeve 110 and shaft 130 in any manner known in the art. In an exemplary embodiment, first end of compressive device 140 includes a larger diameter coil which sits upon ledge 114 of head 112, thereby restricting or minimizing translation of compressive device 140 within sleeve 110. The larger diameter coil may also be further retained by a C-clip or laser welding to sleeve 110 (e.g., at any location within the first end).

Second end of compressive device 140 may include a tang 142. Tang 142 may extend longitudinally from the perimeter of the end coil. Tang 142 may be crimped into a hole in shaft 130, laser welded to the end of shaft 130 and/or any other means for attaching tang 142 to shaft 130. In other embodiments, shaft 130 may abut compressive device 140, compressive device 140 may receive shaft 130 within its coils, or compressive device 140 may abut a component attached to shaft 130. For example, compressive device 140 may be a separate component suitably joined (e.g., welded, glued, molded) to shaft 130 and/or end cap 136.

Locating compressive device 140 inside sleeve 110 is significantly advantageous because the compressive device is fully or partially protected from bone growth over and between the coils which may limit or destroy the functionality of the spring. Similarly, a re-absorbable material is not needed to be inserted between the coils in order to delay the compressive action of the spring. In other words, upon insertion, compressive device 140 is able to provide immediate and subsequent compression. Moreover, because shaft 130 and sleeve 110 rotate along with compressive device 140, bone screw device 100 may be inserted or removed with minimal or no torque or unraveling of compressive device 140.

Figure 10:
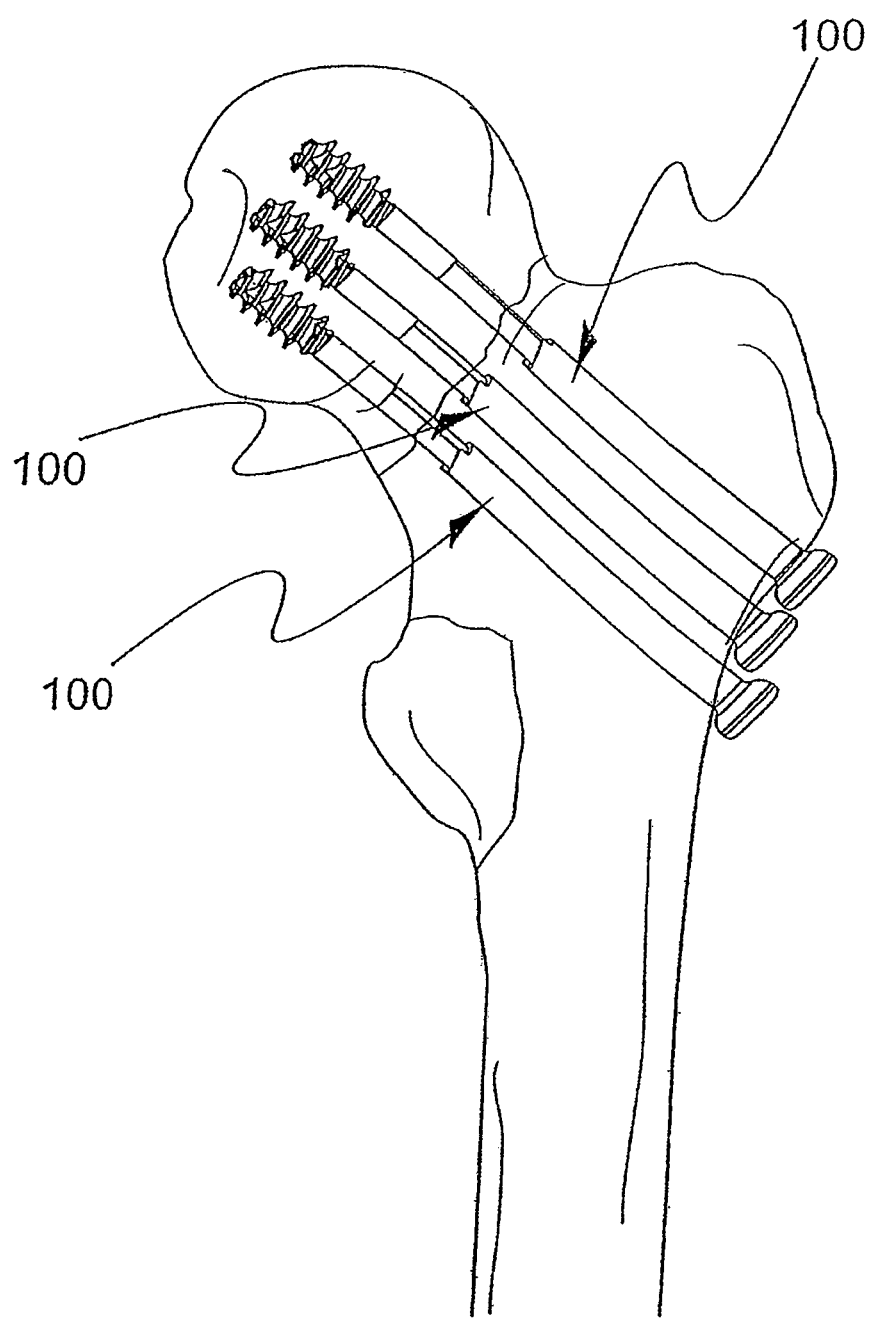
FIG. 10 shows multiple cannulated screws providing rotational stability to a fracture, in accordance with an exemplary embodiment of the present invention.

Multiple bone screws 100 of the present invention may also be used for rotational stability. For example, as set forth in FIG. 10, more than one bone screw (e.g., three) may be used to maintain compression and provide rotational stability in a fracture within the head of the femur bone.

Figure 11:
FIG. 11 shows a cannulated screw received through an intermedulary rod, in accordance with an exemplary embodiment of the present invention.

Bone screw 100 of the present invention may be used in place of any existing bone screw, or any existing component of a product that performs a similar function as a bone screw. With respect to FIG. 11, bone screw 100 is used in association with an intermedulary rod for additional support and stability.

Figure 12:
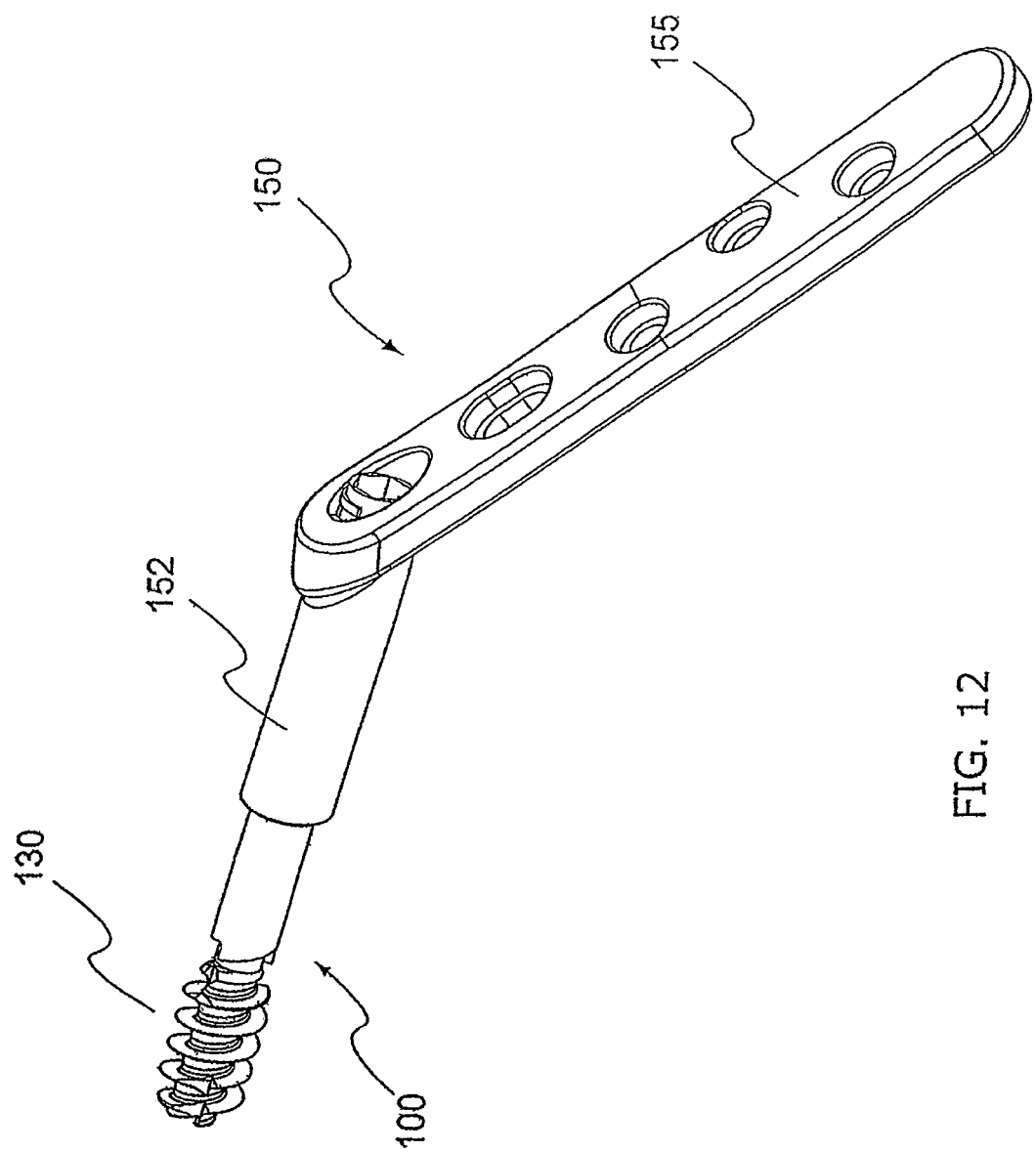
FIG. 12 shows a cannulated screw with a sleeve and a barrel as part of a hip screw plate system, in accordance with an exemplary embodiment of the present invention.

With respect to FIG. 12, bone screw 100 is incorporated into a compression/dynamic hip screw system 150 which may be used on, for example, a proximal femur fracture. An exemplary hip screw system 150 may include any combination of the various compression hip screw plates and nails manufactured by Smith & Nephew. In one embodiment, bone screw 100 is received into barrel 152 of hip screw system 150 in place of the standard bone screw which is typically received into barrel 152. Barrel 152 may or may not include an additional compressive device 140. In another embodiment, barrel 152 may act as a second sleeve 110, thereby adding to the available translation of shaft 130. In other words, shaft 130 translates within sleeve 110, and sleeve 110 itself may translate within barrel 152 before hip screw system 150 protrudes from the bone. In a further embodiment, sleeve 110 is affixed directly to plate 155, so a barrel is not needed.

Hip screw system 150 (with standard plate 155 and cortical bone screws) is inserted as is known in the art, and the features of the present invention incorporated into hip screw system 150 provide additional benefits by minimizing or preventing the device from protruding beyond the bone, and by maintaining an additional amount of compression across the fracture during fracture collapse. A T-Handle may be used to rotate bone screw 100 into the bone. One skilled in the art will appreciate that bone screw 100 may replace or supplement any of the screws (e.g., cortical bone screws, medial fragment screws and/or main bone screw) typically used in association with hip screw system 150.

FIG. 13 shows another embodiment of hip screw system 150, wherein shaft 130 is received directly into barrel 152 of existing hip screw system 150, without the need for a separate sleeve 110. A standard barrel 152 may be used or a longer opening formed within barrel 152 to allow shaft 130 greater translation within barrel 152. Barrel 152 may also include any of the features and functions described above with respect to sleeve 110. For example, barrel 152 may include one or more flat inner portions to complement flat portion 135 of shaft 130, a ledge 114 to hold a wider diameter spring, etc. Any of the hip screw systems may or may not incorporate a compressive device 140 inside sleeve 110 or barrel 152. Without compressive device 140, barrel 152 and/or sleeve 110 is still configured to allow shaft 130 to collapse within barrel 152 and/or sleeve 110, as discussed above.

Compression screw 157 is inserted through plate 155, through barrel 152 and into shaft 130. Upon rotating or translating compression screw 157 through barrel 152, the head of compression screw 157 engages (or abuts) a recessed portion of plate 155 and/or a recessed portion of barrel 152. Upon continuing to rotate compression screw 157, shaft 130 is "pulled" back into barrel 152, thereby causing further compression. In another embodiment, compression screw 157 is also received through compressive device 140 which itself resides in barrel 152 and/or sleeve 110. Upon receiving a weight bearing load, hip screw system 150 allows shaft 130 to translate with minimal or no protrusion of hip screw system 150 beyond the bone, and also, maintaining an additional amount of compression across the fracture during fracture collapse.

With respect to FIG. 14, another exemplary embodiment includes an improved screw 100 having a sleeve 110 and a shaft 130. In one embodiment, no additional elements exist between sleeve 110 and shaft 130, but in other embodiments (as discussed below in more detail and in FIGS. 15 and 17), a compressive device 140 (e.g. split washer) is located between sleeve 110 and shaft 130. In an exemplary embodiment, each of the elements sleeve 110, shaft 130, and compressive device 140 may be cannulated.

In one embodiment, with respect to FIG. 15, shaft 130 includes a first end 132 having a gripping device 133 and a second end 134. Gripping device 133 may include any structure and configuration for enabling shaft to enter and attach to an object. In one embodiment, gripping device includes a threaded surface thereon. The threaded surface may include cutting threads, mating threads, barbs, ribbed surface or any other surface configured to retain shaft 130 into an object. In an exemplary embodiment, gripping device 133 is about 0.63 inches in length with a pitch of about 14.3 threads per inch.

In one embodiment, second end 134 of shaft 130 is configured to restrict shaft 130 from translating beyond a particular location with respect to the sleeve 110. In an exemplary embodiment, end cap 136 is located on or near second end 134, and is formed in a cylindrical configuration such that end cap 136 freely translates within the cylindrical portion of sleeve 110, but end cap 136 stops the translation of shaft 130 when a bottom edge 144 of end cap 136 compresses compressive device 140 against a flat inner surface or ledge 114 of sleeve 110. An exemplary diameter of end cap 136 is about 0.22 inches.

End cap 136 includes a recessed portion for receiving the hex head of a tool. One skilled in the art will appreciate that end cap 136 may be any configuration suitably configured to receive any suitable working tool. The recessed portion is about 0.1 inches in depth and about 0.12 inches wide. End cap 136 may include an axial length that is shorter than the axial length of the cylindrical portion of sleeve 110, such that end cap 136 may move within a range of distance capable of compressing, extending, and moving out of and into communication with compressive device 140 without exiting the chamber of the cylindrical portion of sleeve 110. This range of distance will ensure that compression from the fracture of an object, such as a bone, causing the shaft 130 to move towards the sleeve 110, will not cause the end cap 136 to exit the chamber within the cylindrical portion of sleeve 110, thereby avoiding a protruding end cap 136 from causing injury or inconvenience to a patient or other user of the screw 100. End cap 136 ensures the compression of compressive device 140 so continued compression can be applied against the fracture. End cap 136 may be integral with shaft 130, welded onto shaft 130, or otherwise affixed to shaft 130.

With continued reference to FIG. 15, a head 112 with a diameter wider than the end cap 136 may be located at the first end of sleeve 110. Alternatively, sleeve 110 may not include head 112. Rather, sleeve 110 may merely rest flush with an object, such as a bone, without having any ridge resting on the exterior surface of the object. An exemplary diameter of head 112 is about 0.4 inches. In one exemplary embodiment, head 112 includes a bottom edge 148 that abuts against the exterior surface of an object, such as a bone, bone plate 155 (FIG. 13), or barrel 152. In another embodiment, sleeve 110 may be formed as a barrel 152. Head 112 (or any other portion of sleeve 110) may also include a ledge 114, as previously identified, for retaining compressive device 140 within sleeve 110. Cap 20 (discussed above in other embodiments) may be configured as sleeve 110 (or barrel) and any components of cap 20 may be incorporated into bone screw 100.

A second end of sleeve 110 includes an opening 116 which receives shaft 130 such that shaft 130 is able to at least partially move within sleeve 110, with minimal or no movement of sleeve 110. In an exemplary embodiment, the chamber within the cylindrical portion of the overall sleeve 110 is about 7 mm long, and the overall sleeve 110 is about 0.3 inches wide at the outer diameter, and about 0.21 inches wide at the inner diameter. In an exemplary embodiment, the overall end cap 136 located within the chamber of the cylindrical portion of sleeve 110 is about 2.5 mm long and about 0.21 inches wide at the outer diameter.

In one embodiment, and with respect to FIGS. 16 and 17, a compressive device 140 exists between sleeve 110 and shaft 130 such that compressive device 140 exerts a force directly or indirectly against shaft 130. Compressive device 140 may include, for example, a spring, split washer, or any other element which exerts a force and/or bears a load. In one embodiment, compressive device 140 is located inside sleeve 110 (as discussed above). In a particular embodiment, compressive device 140 is a split washer having about 1 mm of expansion and compression formed in a helical shape. As such, compressive device 140 allows about 1 mm of compression before end cap 136 fully compresses compressive device 140, or, conversely, about 1 mm of extension before end cap 136 fully relaxes compressive device 140. When end cap merely rests against relaxed and fully extended compressive device 140, there is approximately 1 mm of distance between the outer surface of end cap 136 and the outer surface of sleeve head 112. Compressive device 140 is shown either relaxed and in contact with end cap 136 or at least partially compressed in FIG. 17 such that sleeve 110 and shaft 130 are at least in contact with or indirectly exerting force against each other. In its partially compressed state, compressive device 140 permits end cap 136 to recede within the cavity or chamber formed within the cylindrical portion of sleeve 110, as shown in FIG. 16.

Figure 9:
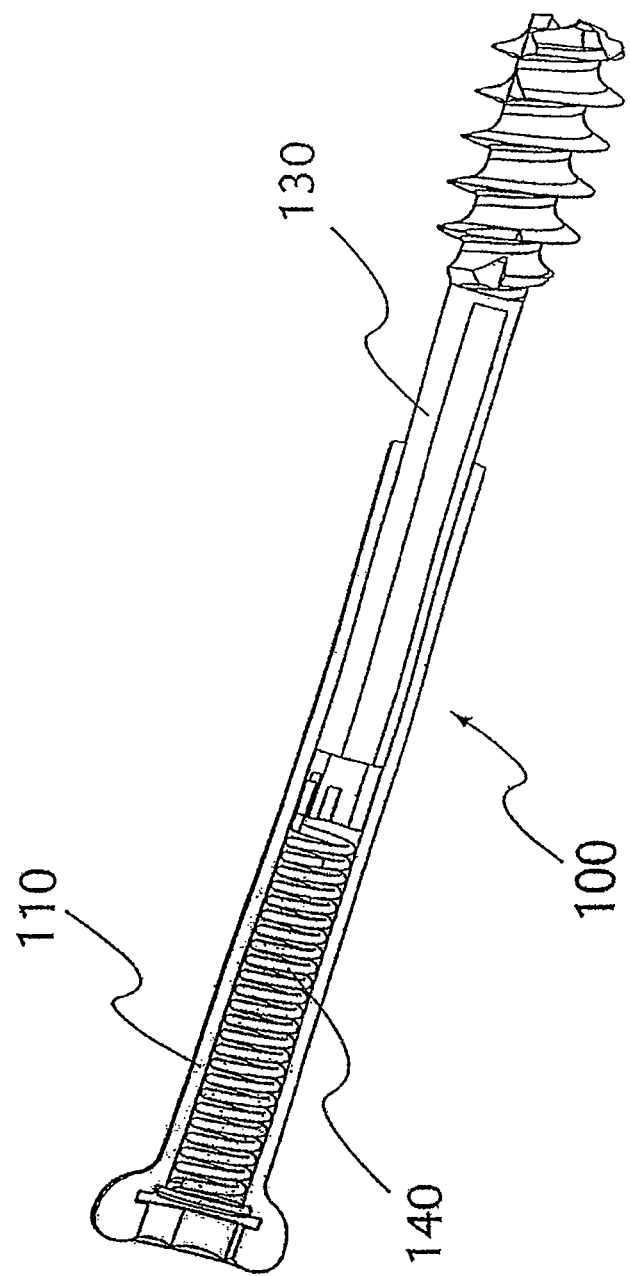
FIG. 9 is a cannulated screw having a sleeve, a compressive device and a threaded shaft and shown after extending the compressive device, in accordance with an exemplary embodiment of the present invention.

Having described exemplary components of the invention, exemplary methods for inserting bone screw 100 will now be described. An exemplary method for inserting bone screw 100 comprises drilling a bore hole into the two objects (e.g., two pieces of the fractured bone) which are to be compressed together. In an exemplary method used in conjunction with the bone screw 100 described with reference to FIGS. 14 through 17, one or more coaxial bore holes may be drilled, having different diameters and depths in order to accommodate the insertion of a sleeve 110 having a wider diameter and shorter depth than a shaft 130 having a narrower diameter and longer depth. A guide rod may be inserted into the bore hole, then bone screw 100 may be inserted over the guide rod. Either head 112 (FIGS. 7 through 9) or end cap 136 (FIGS. 14 through 17), depending upon the embodiment employed, of bone screw 100 is then rotated (e.g. using a drill, hex head driver, or other suitable device) into and through the proximal bone portion or fragment. Head 132 of shaft 130 then enters the distal bone portion or fragment. When sleeve 110 impacts or sits flush against the surface of the proximal bone portion or fragment (or against a plate placed over the bone portion or fragment), either head 112 (FIGS. 7 through 9) or end cap 136 (FIGS. 14 through 17), depending upon the embodiment employed, of sleeve 110 continues to rotate, but sleeve 110 no longer translates into the bone. However, the rotation of sleeve 110 or end cap 136, depending upon the embodiment employed, continues to advance shaft 130 further into the distal bone portion or fragment because threads of gripping device 133 move shaft 130 forward. Such continued translation and penetration of shaft 130 into the distal bone portion or fragment also extends compressive device 140 (as best shown in FIG. 9) or compresses compressive device 140 (as best shown in FIGS. 16 and 17), depending upon the embodiment employed. In other words, the continued advance of shaft 130 causes compressive device 140 to stretch beyond its relaxed condition (as shown in FIG. 9) or compress from its relaxed helical condition towards a flat condition (as shown in FIG. 17). After the bone screw is appropriately inserted, the guide rods are removed.

One skilled in the art will appreciate that shaft 130 may penetrate into the distal bone portion or fragment any desired partial or full distance, and thus, extend or compress, as applicable, compressive device 140 to any desired partial or full extension, compression, or force. One skilled in the art will appreciate that any "rotational insertion" discussed herein may alternatively or additionally include other means for insertion such as, for example, a direct translation using a hammer to force the shaft and/or sleeve into the bone.

After insertion of bone screw 100, compressive device 140 exerts force against sleeve 110 and shaft 130, thereby forcing the components either toward or away from one another, depending upon the embodiment employed. Such force helps to maintain the compressive load at the union of the fracture. As additional compression is exerted on the load in a fracture collapse (e.g., from weight bearing), the bone is compressed closer together, so force may be reduced. However, the present invention either collapses or expands, as applicable, in association with the fracture collapse to substantially minimize or prevent sleeve head 112 of bone screw 100 (FIGS. 7 through 9) from protruding beyond the bone or to substantially minimize or prevent end cap 136 of bone screw 100 (FIGS. 14 through 17) from protruding beyond the chamber within the cylindrical portion of head 112. In other words, sleeve head 112 is substantially maintained against the lateral cortex, while compressive device 140 maintains compression across the fracture during fracture collapse. That is, as the bone portions or fragments undergo stress relaxation, bone screw 100 similarly relaxes, while continuing to hold the portions or fragments together. As such, bone screw 100 continues to accommodate the stress relaxation of the bone portions or fragments until the fracture therebetween has significantly or completely healed.

As discussed above, in one embodiment, compressive device 140 is a spring having about 10 mm of extension. As such, the spring allows about 10 mm of compression before shaft 130 impacts sleeve 110 so that sleeve head 112 is forced away from the cortex. Sleeve head 112 may be maintained against the lateral cortex until a sufficient amount of force no longer exists within compressive device 140, then bone screw 100 may simply act as a traditional bone screw.

As also discussed above, in another embodiment, compressive device 140 is a split washer having about 1 mm of compression. As such, the split washer allows about 1 mm of extension before end cap 136 of shaft 130 moves away from compressive device 140 in a direction towards the exit of the chamber of the cylindrical portion of sleeve 110. Unlike the embodiment discussed with reference to FIGS. 7 through 9, the embodiment discussed with reference to FIGS. 14 through 17 provides an additional advantage of permitting the shaft 130 to move fully exit sleeve 110 without ever forcing sleeve 110 or sleeve head 112 away from the cortex. As with the embodiment discussed with reference to FIGS. 7 through 9, the embodiment discussed with reference to FIGS. 14 through 17 provides a sleeve head 112 that may be maintained against the lateral cortex until a sufficient amount of force no longer exists within compressive device 140, then bone screw 100 may simply act as a traditional bone screw.

The present invention is described herein in connection with the fixation of bone fractures; however, one skilled in the art will appreciate that the lagwire or bone screw system and method described herein may also be used for changing, maintaining, reducing or expanding the distance between objects, object portions, or surfaces, compressing objects or object portions together, or providing pressure to surfaces. For example, the present invention may be used to repair wood products, tree limb damage, breaks in supports or columns, cracks in sculptures or buildings, fractures in sections of concrete or other building materials, cracks or breaks in car parts and/or the like.

In the foregoing specification, the invention has been described with reference to specific embodiments. Various modifications and changes can be made, however, without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. The scope of the invention is accordingly to be limited by nothing other than the appended claims, in which reference to an element in the singular is not intended to mean "one and only one" unless explicitly so stated, but rather "one or more." Moreover, where a phrase similar to 'at least one of A, B, and C' is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. All structural, chemical, and functional equivalents to the elements of the above-described exemplary embodiments that are known to those of ordinary skill in the art are expressly incorporated herein by reference and are intended to be encompassed by the present claims. Further, a list of elements does not include only those elements but may include other elements not expressly listed or inherent to such process, method, article, or apparatus.

The invention claimed is:

1. A fracture compressive system comprising:
   a sleeve comprising a proximal sleeve portion and a distal sleeve portion, wherein the sleeve is configured to contact a first bone portion, wherein the sleeve includes a surface which forms a ridge on the inside surface of the sleeve;
   a stop cap;
   a shaft comprising a distal shaft portion, a proximal shaft portion, and a body portion, wherein an exterior of the distal shaft portion is configured to anchor into a second bone portion, wherein the proximal shaft portion of the shaft is received within the sleeve such that shaft and sleeve move longitudinally relative to one another,
   wherein the stop cap attaches to the proximal shaft,
   wherein the shaft includes a flat surface such that the ridge impacts a distal portion of the stop cap to limit the outward longitudinal movement of the shaft and the ridge impacts a distal portion of the flat surface to limit the inward longitudinal movement of the shaft; and
   a compressive device engaged between the sleeve and the shaft, wherein the proximal end of the sleeve comprises a recessed region comprising a ledge, wherein the compression device has one end abutting the ledge, and wherein the compressive device is configured to shorten in direct relationship with collapse of the shaft relative to the sleeve, and wherein the shaft, the sleeve and the compressive device cannot move rotationally relative to one another.

2. The system of claim 1, wherein the compressive device substantially maintains compression across the fracture during the collapse of the fracture, wherein the shaft is configured to be substantially maintained at least partially within the second bone and at least partially within the sleeve during the collapse of the fracture, until a sufficient amount of force no longer exists within the compressive device.

3. The system of claim 2, wherein the sleeve, the stop cap, the shaft, and the compressive device are cannulated.

4. The system of claim 3, wherein a distance the shaft can travel in the sleeve is greater than a distance the first bone portion and the second bone portion can collapse against one another, such that the shaft is substantially maintained at least partially within the second bone portion and at least partially within the sleeve during a collapse of a fracture.

5. The system of claim 4, wherein the compressive device exerts a force over a longer distance than a collapsible distance between the first bone and the second bone.

6. The system of claim 5, wherein the system acts as a traditional bone screw when a sufficient amount of force no longer exists within the compressive device, wherein the compressive device is located between the sleeve and the shaft, and wherein the compressive device substantially maintains compression across the fracture during the collapse of the fracture.

7. The system of claim 6, wherein the system acts as a traditional bone screw in response to the shaft collapsing into the sleeve, wherein the shaft extends away from the compressive device.

8. The system of claim 7, wherein the sleeve is configured with threads on an outside surface of the sleeve to facilitate rotating the sleeve at least partially into the first bone portion.

9. The system of claim 8, wherein the compressive device is fully enclosed within the sleeve and configured to at least one of: exert a distal force against the sleeve and resist proximal movement of the sleeve.

10. The system of claim 1, wherein the compressive device is a helical spring.

11. The system of claim 1, wherein a distal end of the compressive device includes a tang fixedly attached to the stop cap.

* * * * *